United States Patent [19]
Griffin et al.

[11] Patent Number: 5,965,435
[45] Date of Patent: Oct. 12, 1999

[54] VIRAL NUCLEOTIDE SEQUENCES

[75] Inventors: Annette Mary Griffin; Louis Joseph Norman Ross; Simon David Scott; Matthew McKinley Binns, all of Huntingdon, United Kingdom

[73] Assignee: Rhone Merieux S.A., Lyons, France

[21] Appl. No.: 08/460,257

[22] Filed: Jun. 2, 1995

Related U.S. Application Data

[62] Division of application No. 08/125,039, Sep. 22, 1993, which is a continuation of application No. 07/669,391, filed as application No. PCT/GB89/01075, Sep. 13, 1989, abandoned.

[30] Foreign Application Priority Data

Sep. 13, 1988 [GB] United Kingdom .................... 8821441

[51] Int. Cl.⁶ ............................. C12N 15/38; C12N 15/86
[52] U.S. Cl. ...................................... 435/320.1; 536/23.72
[58] Field of Search ...................... 424/229.1; 435/172.3, 435/320.1; 514/44; 536/23.72

[56] References Cited

PUBLICATIONS

Bagust et al. (1995) Avian infectious laryngotracheitis: virus–host interactions in relation to prospects for eradication. Avian Pathol. 24:373–391.

Wilkinson et al. (1995) Gene therapy and viral vaccination: the interface. British Med. Bull. 51:205–216, Jan. 1995.

*Primary Examiner*—Nancy Degen
*Assistant Examiner*—Robert Schwartzman
*Attorney, Agent, or Firm*—Larson & Taylor

[57] ABSTRACT

Various genes of herpes virus of turkeys (HVT), Marek's disease virus (MDV) and infectious laryngotracheitis virus (ILTV) have been identified as non-essential regions (and candidates for insertion sites for foreign genes) and/or as antigen-encoding regions. The former include the HVT homologue of the HSV (herpes simplex virus) gC gene, the TK (thymidine kinase) region of MDV or ILTV, ORF3 of ILTV (as defined herein), the ribonucleotide reductase (large subunit) gene of ILTV, MDV or HVT and the ribonucleotide reductase (small subunit) gene of MDV. The antigen-encoding regions include the HVT homologues of the HSV gB, gC and gH genes, the ILTV homologue of HSV gB, ORF2 of ILTV, and the HVT homologue of the HSV-1 immediate early genes IE-175 and IE-68. Manipulation of these genes allows vaccines to be prepared comprising attenuated virus or virus carrying heterologous antigen-encoding sequences.

4 Claims, 67 Drawing Sheets

FIG 2A

TCGAGCTCGCGCGGGATGTTAGTCACGATAGACATCGGT
          10        20        30        40

TCGCCCAGCCGTCGAATACAGCATTATATTTTAGTGTTG
          50        60        70        80

AAAATGTAGGCTGCTTCCTCACTTAAAGGAGAAATGGCT
          90       100       110       120

CGATTCATGTTTCATAGCAGTAGAAAACAGATTGGACCG
         130       140       150       160

TCAGTAAGTTTAGAGGGTTTTATGACTTTAGCACTATAGA
         170       180       190       200

TAATGTAACTCGGCCCATCGCCATGGCTTGGAAATATATC
         210       220       230       240

AAAGAACTGATTTTTGCAACAGCTTTATTTTCTTCTGTAT
         250       260       270       280

TTAAATGTGGCGAATTGCACATCTGTCGTGCCGACAGTTT
         290       300       310       320

GCAGATCAACAGCAATGGAGACTATGTGTATGAAAAATGA
         330       340       350       360

FIG 2B

```
ATATATATAACATATGAAACCGAATATCCACTTATAATGA
        370       380       390       400
TTCTGGGTCAGAATCAAGCACTTCAGAAACGCAAAATAT
        410       420       430       440
GACTGCAATTATTGATACAGATGTTTTTCGTTGCTTTAT
        450       460       470       480
TCTATTTTGCAGTATATGGCCCCCGTTACGGCAGATCAGG
        490       500       510       520
TGCGAGTAGAACAGATTACCAACAGCCACGCCCCCATCTG
        530       540       550       560
ACCCGTCCAATATTCTTGTGTCCCTGCATTTTATCTCACA
        570       580       590       600
                                    M  H
CAATTTATGAACAGCATCATTAAGATCATCTCACTATGCA
        610       620       630       640
 Y  F  R  R  N  C  I  F  F  L  I  V  I
CTATTTTAGGCCGAATTGCATTTTTTCCTTATAGTTATT
        650       660       670       680
```

FIG 2C

```
L  Y  G  T  N  S  S  P  S  T  Q  N  V  T
CTATATGGTACGAACTCATCTCCGAGTACCCAAAATGTGA
          690         700        710        720

S  R  E  V  V  S  S  V  Q  L  S  E  E
CATCAAGAGAAGTTGTTTCGAGCGTCCAGTTGTCTGAGGA
          730         740        750        760

E  S  T  F  Y  L  C  P  P  P  V  G  S
AGAGTCTACGTTTTATCTTTGTCCCCACCAGTGGGTTCA
          770         780        790        800

T  V  I  R  L  E  P  P  R  K  C  P  E  P
ACCGTGATCCGTCTAGAACCGCGAAAATGTCCCGAAC
          810         820        830        840

R  K  A  T  E  W  G  E  G  I  A  I  L
CTAGAAAAGCCACCGAGTGGGTGAAGGAATCGGATATTA
          850         860        870        880
```

FIG 2D

```
      F   K   E   N   I   S   P   Y   K   F   K   V   T
      TTTAAAGAGAATATCAGTCCATATAAATTTAAAGTGACGC
      |||   ||||||||||||||||||||||   ||||||||
      GAGAATATCAGTCCGTATAAATTCAAAGTAACAC
              890        900       910        920

L   Y   Y   K   N   I   I   Q   T   T   T   W   T   G
      TTTATTATAAAATATCATTCAGACGACGACATGGACGG
      ||||   |||||||   ||   |||||||||||||||
      TTTACTATAAGAACGTTATACAAACTACGACGTGGACTG
                 930       940        950       960

T   T   Y   R   Q   I   T   N   R   Y   T   D   R
      GGACGACATATAGACAGATCACTAATCGATATACAGATAG
      ||||||||   ||||   |||   ||||   |||||||||
      GGACGACGTACAGACAGATAACAGTATACAGATAG
                970        980       990       1000
```

FIG 2E

```
       T  P  V  S  I  E  E  I  T  D  L  I  D
     GACGCCCGTTCCATTGAAGAGATCACGGATCTAATCGAC
     ||||| || || || ||| || ||| ||| ||| || ||
     AACACCCGTGTCTATCGACGAAATTACTGATTTGATAGAT
            1010      1020      1030      1040

G  K  G  R  C  S  S  K  A  R  Y  L  R  N
     GGCAAAGGAAGATGCTCATCTAAAGCAAGATACCTTAGAA
     ||  || || ||| ||| |||||| |||||  ||| || |
     GGTAAGGGGAAATGTTCATCCAAAGCCCGTATCTTCG
          1050      1060      1070      1080

N  V  Y  V  E  A  F  D  R  D  A  G  E
     ACAATGTATATGTTGAAGCCGTTTGACAGGGATGCGGGAGAA
            1090      1100      1110      1120

K  Q  V  L  L  K  P  S  K  F  N  T  P
     AAACAAGTACTTCTAAAACCATCAAAATTCAACACGCCC
            1130      1140      1150      1160
```

FIG 2F

```
       E  S  R  A  W  H  T  T  N  E  T  Y  T  V
      GAATCTAGGGCATGGCACGACTAATGAGACGTATACCG
      |||||||||| |||| ||  ||||||||| |||||| ||
      GGCATGGCATACGACCAACGAGACGTACACCG
              1170      1180      1190      1200

——————V——————
       W  G  S  P  W  I  Y  R  T  G  T  S  V
      TGTGGGATCACCATGGATATCGAACGGAACCTCCGT
      ||||||||  || ||||| |||| ||||||  ||||||
      TGTGGGATCTCCATGGTATATAGAACGGCACGTCCGT
              1210      1220      1230      1240

———A———
       N  C  I  V  E  E  M  D  A  R  S  V  F
      CAATTGTATAGTAGAGGAAATGGATGCCCGTCTGTGTTT
      ||| || |||||| ||||||||| ||||||| ||| |||
      CAACTGCATAGTAGAAGAGATGGATGCCAGATCAGCATTT
              1250      1260      1270      1280
```

FIG 2G

```
          ---T---                                                                                         
   P   Y   S   Y   F   A   M   A   N   G   D   I   A   N
   CCGTATTCATATTTGCAATGGCCAATGGGCGACATCGCGA
   ||| ||  ||||||||||||||||||||| || |||||
   CCATACACGTACTTTGCAATGGCCAATGGAGATATCGCAA
       1290        1300        1310        1320

---M---              ---T---T---D---
       I   S   P   F   Y   G   L   S   P   P   E   A   A
   ACATATCTCCATTTTATGGTCTATCCCACCAGAGGCTGC
   ||||  ||||||||| ||  || || |||| ||| || ||
   ACATGTCTCCATTTTATGGAACAACTCCAACCGACGCGGC
       1330        1340        1350        1360

---S---                 ---R---R---
       A   E   P   M   G   Y   P   Q   D   N   F   K   Q
   CGCAGAACCCATGGGATATCCCCAGGATAATTTCAAACAA
   ||| || |||||| ||||||  |||| ||||| || |||
   CGCGGAGCCCATGAGCTATCCGCAAGACCGATTCAGGCAA
       1370        1380        1390        1400
```

FIG 2H

```
       F               P                    T
    L  D  S  Y  F  S  M  D  L  D  K  R  R  K
    CTAGATAGCTATTTTCAATGGATTTGGACAAGCGTCGAA
    ||| ||||||  |||||||||||||| ||| ||||||||
    TTTGACAGCTATTCCCATGGATTTGGATACGGCCCGAA
           1410       1420       1430       1440

A  S  L  P  V  K  R  N  F  L  I  T  S
    AAGCAAGCCTTCCAGTCAAGCGTAACTTTCTCATCACATC
    ||
    AA       1450       1460       1470       1480

H  F  T  V  G  W  D  W  A  P  K  T  T
    ACACTTCACAGTTGGGTGGACTGGGCTCCAAAAACTACT
              1490       1500       1510       1520

R  V  C  S  M  T  K  W  K  E  V  T  E  M
    CGTGTATGTTCAATGACTAAGTGGAAAGAGTGACTGAAA
              1530       1540       1550       1560

L  R  A  T  V  N  G  R  Y  R  F  M  A
    TGTTGCCGTGCAACAGTTAATGGGAGATACAGATTTATGGC
              1570       1580       1590       1600
```

FIG 21

R E L S A T F I S N T T E
CCGTGAACTTCGCAACGTTTATCAGTAATACGACTGAG
      1610      1620      1630      1640

F D P N R I I L G Q C I K R
TTTGATCCAAATCGCATCATATTAGGACAATGTATTAAAC
      1650      1660      1670      1680

E A E A A I E Q I F R T K
GCGAGGCAGAAGCAGCAATCGAGCAGATATTTAGGACAAA
      1690      1700      1710      1720

Y N D S H V K V G H V Q Y
ATATAATGACAGTCACGTCAAGGTTGGACATGTACAATA
      1730      1740      1750      1760

F L A L G G F I V A Y Q P V
TTTCTTGGCTCTCGGGGATTTATTGTAGCATATCAGCCTG
      1770      1780      1790      1800

L S K S L A H M Y L R E L
TTCTATCCAAATCCCTGGCTCATATGTACCTCAGAGAATT
      1810      1820      1830      1840

FIG 2J

```
  M   R   D   N   R   T   D   E   M   L   D   L   V
GATGAGAGACAACAGGACCGATGAGATGCTCGACCTGGTA
        1850        1860        1870        1880
  N   N   K   H   A   I   Y   K   K   N   A   T   S   L
AACAATAAGCATGCAATTTATAAGAAAAATGCTACCTCAT
        1890        1900        1910        1920
  S   R   L   R   R   D   I   R   N   A   P   N   R
TGTCACGATTGCGGGGAGATATTCGAAATGCACCAAATAG
        1930        1940        1950        1960
  K   I   T   L   D   D   T   T   A   I   K   S   T
AAAAATAACATTAGACGACACCACAGCTATTAAATCGACA
        1970        1980        1990        2000
  S   S   V   Q   F   A   M   L   Q   F   L   Y   D   H
TCGTCTCTGTTCAATTCGCCATGCTCCAATTTCTTTATGATC
        2010        2020        2030        2040
  I   Q   T   H   I   N   D   M   F   S   R   I   A
ATATACAAACCATATTAATGATATGTTTAGTAGGATTGC
        2050        2060        2070        2080
```

FIG 2K

```
          T  A  W  C  E  L  Q  N  R  E  L  V  L
          CACAGCTTGGTGCGAATTGCAGAATAGAGAACTTGTTTA
                 2090      2100      2110      2120

W  H  E  G  I  K  I  N  P  S  A  T  A  S
          TGGCACGAAGGATAAAGATTAATCCTAGCGCTACAGCGA
              2130      2140      2150      2160

A  T  L  G  R  R  V  A  A  K  M  L  G
                                    GTGCAACATTAGAGAAGGAGAGTGGCTGCAAAGATGTTGG
                                                                 ||| || ||||||| ||
                                                                 GCCAAAATGTTGG
                                        2170      2180      2190      2200

——D——                              ——I——E——T——S—
          D  V  A  A  V  S  S  C  T  A  I  D  A
          GGATGTCGCTGCTGTATCGAGCTGCACTGCTATAGATGCG
          ||| ||| |||      || ||||| ||  ||   |||
          TGACGATGCCGCGTATCATCATGTATTGAGACTGATTCA
              2210      2220      2230      2240
```

FIG 2L

```
       -D-                                           -V-
       E   S   V   T   L   Q   N   S   M   R   V   I   T   S
       GAATCCGTCACTTTGCAAAATTCTATGGGAGTTATCACAT
       ||  ||||  ||  |||||||| ||||||||||  ||  ||||||||
       GATTCTGTTACCTTACAAAATTCCATGCGGGTTGTCACCT
                 2250          2260          2270          2280

T   N   T   C   Y   S   R   P   L   V   L   F   S
       CCACTAATACATGTTATAGCCGACCATTGGTTCTATTTC
       |||  ||||||||| ||||||||||||||  ||  ||  ||
       CTACCAATACTTGTGTTATAGCCGCCCTTTAGTGTTATTCTC
                 2290          2300          2310          2320

--D--R----D--K-----                              G
       Y   G   E   N   Q   G   N   I   Q   Q   L   G
       ATATGGAGAAAACCAAGGAAACATACAGGGACAACTCGGTG
       ||||  ||  ||||||||  ||||  ||||  ||||||  |||
       CTACGGGGACCGACAAGACAAAATACAAGGACAGAGTTGGGG
                 2330          2340          2350          2360
```

FIG 2M

```
                        I                       I
E  N  N  E  L  L  P  T  L  E  A  V  E  P
AAAACAACGAGTTGCTTCCAACGCTAGAGGCTGTAGAGC
||||||  || ||  |||||| |||||||  ||||||
AAAACAATGAATTGATTCCAACTCTAGAGGCCATAGAGC
         2370       2380       2390    2400

I
   C  S  A  N  H  R  R  Y  F  L  F  G  S
CATGCTCGGCTAATCATCGTAGATATTTCTGTTTGGATC
|||  ||||| |||||  ||||||||||||||
CATGTTCGGCCAATCATCGTAGA
         2410       2420       2430    2440

G  Y  A  L  F  E  N  Y  N  F  V  K  M
CGGTTATGCTTTATTTGAAAACTATAATTTGTTAAGATGG
         2450       2460       2470    2480

V  D  A  A  D  I  Q  I  A  S  T  F  V  E
TAGACGCTGCCGATATACAGATTGCTAGCACATTTGTCG
         2490       2500       2510    2520
```

FIG 2N

```
  L   N   L   T   L   L   E   D   R   E   I   L   P
AGCTTAATCTAACCCTGCTAGAAGATCGGAAATTTGCC
     2530      2540      2550      2560

L   S   V   Y   T   K   E   E   L   R   D   V   G
TTTATCCGTTTACACAAAGAAGAGTTGCGTGATGTTGGT
    2570      2580      2590      2600

V   L   D   Y   A   E   V   A   R   R   N   Q   L   H
GTATTGGATTATGCAGAAGTAGCTCGCCGCAATCAACTAC
    2610      2620      2630      2640

E   L   K   F   Y   D   I   N   K   V   I   E   V
ATGAACTTAAATTTTATGACATAAACAAAGTAATAGAAGT
    2650      2660      2670      2680

D   T   N   Y   A   F   M   N   G   L   A   E   L
GGATACAAATTACGCGTTTATGAACGGTTTGGCCGAATTG
    2690      2700      2710      2720

F   N   G   M   G   Q   V   G   Q   A   I   G   K   V
TTTAACGGTATGGGTCAGTAGGCAAGCTATAGGCAAAG
    2730      2740      2750      2760
```

FIG. 2∅

```
        V  V  G  A  A  G  A  I  V  S  T  I  S
        TTGTAGTAGGGGCTGCCGTGCAATCGTATCTACCATATC
          2770        2780        2790        2800

G  V  S  A  F  M  S  I  P  L  G  L  S
        TGGTGTCTCTGCTTTCATGTCAATCCCTTTGGGGCTTTCG
          2810        2820        2830        2840

A  I  G  L  I  I  I  A  G  L  V  A  A  F
        GCAATCGGTTTAATCATTATAGCAGGACTCGTGGCTGCAT
          2850        2860        2870        2880

L  A  Y  R  Y  V  N  K  L  K  S  N  P
        TTTTAGCATATCGTTATGTAAACAAGCTTAAAGCAATCC
          2890        2900        2910        2920

M  K  A  L  Y  P  M  T  T  E  V  L  K
        AATGAAAGCCCTTTATCCTATGACAACAGAAGTGCTTAAG
          2930        2940        2950        2960

A  Q  A  T  R  E  L  H  G  E  E  S  D  D
        GCACAGGCAACGCGTGAGTTGCATGGCGAGGAATCAGATG
          2970        2980        2990        3000
```

FIG 2P

```
                 L   E   R   T   S   I   D   E   R   K   L   E   E
             ATTTGGAACGAACATCTATTGATGAAAGAAAATTAGAAGA
                     3010        3020        3030        3040

A   R   E   M   I   K   Y   M   A   L   V   S   A
AGCTAGAGAAATGATAAAATATATGGCGTTAGTCTCCGCG
        3050        3060        3070        3080

E   E   R   H   E   K   K   L   R   R   K   R   R   G
GAAGAACGCCACGAGAAAAACTGCGGAAGAAGAGGCGAG
        3090        3100        3110        3120

T   T   A   V   L   S   D   H   L   A   K   M   R
GCACTACCGCCGTTCTATCGGACCACCTGGCAAAAATGAG
        3130        3140        3150        3160

I   K   N   S   N   P   K   Y   D   K   L   P   T
GATTAAAAATAGTAACCCTAAATATGATAAGTTACCTACT
        3170        3180        3190        3200

T   Y   S   D   S   E   D   D   A   V   *
ACATATTCAGACTCAGAAGATGATGCTGTGTAAGTGGGCA
        3210        3220        3230        3240

CTATTATATTTGAACTGAATAAAACGCATAGAGCATGATA
        3250        3260        3270        3280
```

FIG 2Q

```
TGGTTTACTCATTTATTGCGAGATATAAAGCATATTCAAT
     3290      3300      3310      3320
ACGATATATTGCGAACGTGATGCTAAAAACATAGCTCCCT
     3330      3340      3350      3360
GTATTATTGATGCGCCATCATTTGATTAATAAATACATCG
     3370      3380      3390      3400
ACGCCGGCCATCACTGGTGCGGTGTATACCAGCTACGGCGC
     3410      3420      3430      3440
TAGCCATTCATGGTATCCCGTGATTGCTCGATGCTTTCCTT
     3450      3460      3470      3480
CTGAATTCCGTCGGAACGCTCCTGAGAGATGGTCGCAGTT
     3490      3500      3510      3520
ATTGGTACATTTCGACCAGCCTCCGGATCTGAAACTGGCA
     3530      3540      3550      3560
CAGGAATGCACCGTGAATTGTAGAAGTTTTCCTTCCG
     3570      3580      3590      3600
```

FIG 2R

TGGAAGGCATAGGCGTTCGACTCCCATGGGCCATGAAACTGTGGGATGT
3610      3620      3630      3640      3650

FIG 4A

```
TATTATTGGTCCATGCTAGAATAGTCATACGCTACGATCT
         10        20        30        40
GTTGCTATATGACTATCGCCAAACTGTTAAACCCGCGA
         50        60        70        80
AGAATATATTTCATATAAACCTAAGGGCCCCTCAGTCTGA
         90       100       110       120
                              M  K  F  Y  C  L
TTTTTTGTGAAAACGTGTATACCATGAAGTTTTACTGCCT
        130       140       150       160
  I  R  F  M  I  I  A  N  L  Y  S  S  Y
AATCCGTTTCATGATCATAGCGAATCTTTATTCATCTTAC
        170       180       190       200
  Q  I  S  L  P  G  T  Y  P  S  Q  I  L  L
CAAATATCGCTTCCAGGCACATATCCATCGCAAATATTGC
        210       220       230       240
  D  M  K  N  S  P  L  V  R  F  N  I  S
TTGACATGAAGAACTCGCCGCTCGTACGCTTTAATATATC
        250       260       270       280
```

FIG 4B

```
  T   R   D   Y   K   D   E   T   L   W   I   R   K
GACGCGTGATTATAAAGACGAGACACTCTGGATACGGAAA
         290         300         310         320

N   S   T   F   V   Y   I   D   T   A   V   T   T   A
AATTCGACATTTGTTTATATCGATACGGCTGTGACGACAG
         330         340         350         360

N   V   I   F   Y   L   P   I   G   Q   V   R   Q
CGAACGTTATCTTTTTATCTGCCGATCGGTCAGGTACGACA
         370         380         390         400

M   V   F   F   K   R   P   I   S   R   L   L   T
AATGGTTTTTTTCAAGCGTCCAATATCCAGGCTACTAACG
         410         420         430         440

S   N   N   L   V   K   F   I   N   T   G   S   Y   A
TCCAATAACCTGGTTAAATTTATTAATACCGGTTCATACG
         450         460         470         480

N   H   F   K   T   E   L   S   P   Y   L   S
CCAATCATACATTCAAGACAGAACTTTCACCCTATTTGTC
         490         500         510         520
```

FIG 4C

```
  K   T   N   T   P   L   K   K   Y   E   I   V   V
GAAAACCAATACACCGTTGAAGAAATATGAAATTGTTGTC
         530             540             550             560

D   Q   P   T   G   E   N   P   P   A   G   F   G   S
GATCAACCTACTGGAGAGAAACCCTCCGGCAGGGTTCGGAA
         570             580             590             600

L   K   P   A   D   F   L   N   P   G   Y   K   F
GTTTAAAACCGGCAGACTTTCTCAACCCCGGATACAAGTT
         610             620             630             640

V   L   T   S   E   L   V   G   A   Y   T   K   R
CGTTCTCACAAGCGAGTTGGTAGGAGCCTACACAAAACGA
         650             660             670             680

S   C   F   V   D   P   M   D   S   L   V   P   I   D
TCTTGTTTTGTCGATCCGATGGATTCTCTCGTCCCGATAG
         690             700             710             720

Y   D   H   V   R   T   I   I   F   G   S   A   G
ATTATGATCATGTACGAACCATTATATTCGGATCTGCTGG
         730             740             750             760
```

FIG 4D

```
      M   E   I   L   M   K   M   G   I   T   L   A   S
GATGGAGATTTAATGAAGATGGGAATTACTTTGGCATCT
          770           780           790           800

M   T   I   S   T   K   Y   N   P   P   I   E   L   I
ATGACCATTTCGACGAAATATAATCCTCCTATTGAACTGA
          810           820           830           840

I   S   A   K   Y   R   N   L   S   L   L   W   P
TAATATCTGCAAAGTACCGAAATTTATCACTGTTGTGGCC
          850           860           870           880

P   R   Q   Q   Y   E   P   V   N   K   G   T   G
ACCCCGACAACAATATGAACCTGTAAATAAAGGGACTGGA
          890           900           910           920

R   P   H   W   I   Y   L   L   G   V   Y   R   N   V
CGCCCCCATTGGATCTACCTATTAGGTGTGTATAGAAACG
          930           940           950           960

S   D   S   E   R   D   S   Y   M   N   M   I   K
TTTCGGACTCCGAGCGTGACTCATACATGAATATGATTAA
          970           980           990          1000
```

FIG 4E

```
  S   L   G   D   S   M   D   Y   H   F   L   I   S
GAGTCTGGGCGATTCCTATGGATTATCACTTCCTAATTAGC
        1010        1020        1030        1040

R   A   H   A   Q   M   L   I   L   A   A   E   D   R
AGAGCCGCATGCCCAGATGCTGATACTGGCAGCAGAGGACC
        1050        1060        1070        1080

L   V   D   E   M   H   S   F   R   N   V   I   A
GGCTCGTGGATGAAATGCATAGTTTCAGGAACGTTATTGC
        1090        1100        1110        1120

R   L   F   V   S   L   F   A   F   I   R   N   A
GCGTTTATTTGTATCGTTGTTCGCATTCATACGTAACGCA
        1130        1140        1150        1160

F   Q   S   G   Y   T   S   L   N   D   I   I   E   I
TTTCAGTCTGGCTACACCTCTCTTAATGACATAATTGAAA
        1170        1180        1190        1200

E   A   D   L   R   L   I   V   E   G   I   S   S
TCGAAGCCGATTTGAGGTTAATTGTAGAAGGCATTTCTTC
        1210        1220        1230        1240
```

FIG 4F

```
A   A   F   R   K   D   A   S   T   H   F   L   L   I
TGCTGCATTTCGTAAAGACGCTAGTACACACTTTCTTATA
        1250        1260        1270        1280

S   G   T   P   I   K   D   S   K   A   D   L   I   K
TCGGGAACGCCCATAAAAGATAGCAAAGCGGATTTAATTA
        1290        1300        1310        1320

S   L   L   S   K   V   I   R   P   I   S   G   H
AATCGTTGTTGTCTAAAGTCATTCGACCAATTTCCGGACA
        1330        1340        1350        1360

T   R   P   L   S   A   I   Q   H   L   F   L   L
TACACGTCCCTTATCTGCGATACAACATCTATTCCTTTTG
        1370        1380        1390        1400

R   S   A   Y   A   L   D   I   P   R   Q   N   G   S
AGATCCGCTTATGCATTGGATATACCCCGTCAAAACGGAT
        1410        1420        1430        1440

L   S   E   Q   V   S   T   V   A   L   S   F   I
CTTTGAGCGAACAGGTATCTACAGTGGCACTGTCGTTCAT
        1450        1460        1470        1480
```

FIG 4G

```
  E   N   I   H   S   E   A   M   R   D   I   L   S
TGAAAATATTCACAGGCGAGGCCATGAGGGACATTCTGTCA
         1490        1500        1510        1520

W   N   T   T   K   H   A   L   Y   Y   A   F   A
TGGAACACTACAAACAAAGCATGCCGTTGTATTATGCATTCG
         1530        1540        1550        1560

S   I   L   Q   R   P   L   T   E   W   G   A   S
CGAGTATTTTGCAACGGCCACTGACCGAATGGGGCGCCCTC
         1570        1580        1590        1600

R   N   A   R   R   A   I   L   L   A   S   S   M
AAGAAAATGCACGGAGGCAATACTATTAGCATCATCGATG
         1610        1620        1630        1640

C   T   E   E   H   V   I   A   T   E   L   A   I   Q
TGTACAGAAGAGCATGTTATCGCAACTGAGTTGGCTATTC
         1650        1660        1670        1680

E   L   Y   V   K   I   R   S   N   A   D   P   I
AAGAAACTGTATGTCAAAATCAGAAGTAATGCCGACCCAAT
         1690        1700        1710        1720
```

FIG 4H

```
  H   L   L   D   V   Y   T   P   C   L   S   S   L
ACACCTTCTAGACGTATATACACCATGTCTCTTTCTTCACTA
         1730          1740          1750          1760

R   L   D   L   S   E   H   H   R   I   Y   A   M   A
CGATTGGACCTTTCCGAACACCATCGGATATACGCAATGG
         1770          1780          1790          1800

D   V   V   F   Y   P   D   I   Q   Q   Y   L   K
CAGATGTAGTTTTCTATCCAGACATTCAGCAGTATTTGAA
         1810          1820          1830          1840

K   K   S   H   E   G   N   M   K   E   D   D   L
AAAAAAATCCCATGAGGGTAATATGAAGGAAGATGATCTC
         1850          1860          1870          1880

E   T   K   A   E   Y   I   L   T   K   L
GAAACAAAGGCGGAATACATCCTCACCAAGCTT
         1890          1900          1910
```

FIG 5A

```
AAGCTTTTTAGTAAAAACGATTATGACCACCGGACACCCGCT
         10        20        30        40
TTTAGCAATCCTGCCATAAGGTGGTTTCCCGGTGCTTGC
         50        60        70        80
CTCGAAGACAATTGCCAGCTAATCCAGCATTACCATATTT
         90       100       110       120
                            ┌──S──Q
                             M  A  L  P
CCTTGGCTCTGCATTTGGATCTGCCGGTCGATGGCATTGCC
                             |||||||
                             ATGGCATCTCA
        130       140       150       160

──M──T──S──A──Q──I──
  R  R  P  P  T  L  T  R  V  V  Y  L  D  G
GAGAAGACCGCCCACGTTAACGCGAGTTTATCTAGACGGA
  |  |  |  |  |  |  |  |  |  |  |  |  |  |
GATGACATCTGCACAGCTCATACGTGTATACCTCGATGA
        170       180       190       200
```

FIG 5B

```
    —S——M—————————M————————E——I—
     P  F  G  I  G  K  T  S  I  L  N  A  M  P
    CCGTTTGGTATAGGCAAACGTCTATACTAAACGCTATGC
     |  ||||||  |||||||  ||  |||  |  ||  ||
    TCAATGGGTATAGGTAAACGTCAATGTTGAATGAGATAC
            210         220         230         240

———T———L|
     D  H  T  P  D  G  A  P  I  L  K  V  Y
    CCGACCACACGCCCCGATGGGCCTCCTATATTGAAAGTGTA
     ||                                    ||
    CGACGCATCTT
            250         260         270         280

E  P  M  K  Y  W  R  C  Q  S  T  D  L
    CGAACCAATGAAATATTGGAGATGCCAGTCTACCGATTTG
            290         300         310         320
```

FIG 5C

```
                          |————R——|
        V V A A N E T P E R R R G G
        GTGGTAGCTGCCAACGAAACGCCAGAACGTAGGCGTGTG
         ||||—|||||||||||||||—||—||
                          ATCGTCGTCGCAGGG
        330       340       350       360

|——E——F——|          |——L——|        |——S——|       |——V——T——A|
 A  L  S  G  F  Q  S  D  M  I  M  A  S
GAGCTTTATCACGATTCCAATCTGACATGATCATGGCATC
||| ||—|||||—||| |||||—|||||| ||—||  ||—
GAGAGTTTCTTTATTCAATCTAGCATGATGTAACAGC
        370       380       390       400

|——L——S——K——|              |——V——|
 I  Q  A  R  F  A  D  P  Y  L  L  F  H
TATACAAGCCAGATTGCCGATCCATATTGCTTTTCAC
|—||||| ||—| |||||—|||| |||—|—|||||
TTTACAATCAAAGTTGCAGATCCCTATCTTGTATTCAT
        410       420       430       440
```

FIG 5D

```
        H-R-I-T-G-T-R
E R L S S K C R G K I E I C
GAACGGTTATCATCTAAATGTAGAGGAAAAATAGAAATAT
   ||  ||||  || |||  ||||||||||  |||||
GAGCGCTTATCGTCGAAGTGTCATCGCATAACAGGAACAC
    450      460       470       480

G---N----S---L------I
D T P A I I L M L D R H P
GCGATACTCCAGCAATTATATATTAATGCTGGATAGGCACCC
  ||| |||||||||| ||| |||| ||| ||||   ||
GTGGCAATCCATCGCTTATATATTAATTCTAGATCGACATCC
      490       500       510       520

--I---S----T---V-------A----H---
V A A I L C F P I T R Y L
TGTGGCGGATATTATGTTTCCAATCACTCGCTATTTA
 |

FIG 5E

```
         -T---- -D--C-                                  -M-
          L  G  E  Y  S  L  E  M  L  I  S  S  I  I
         CTTGGAGAATATTCTTTGGAAATGTTGATTAGCTCTATAA
         |||||||||||||||||||  ||||||||||  |||| 
         ACTGGAGATTGTTCCTTGGAGATGCTAATTAGTATGATAA
              570       580       590       600

-Q-----P-                   -V--I-
          R  L  P  L  E  S  P  G  C  N  L  T  V
         TAAGACTTCCGTTGGAATCCCCGGATGCAACCTGACAGT
         |||| |||||  |||||| ||  |||||||||||| |||
         TAAGGTTGCCCCAGGAACCGCCAGGATGCAACTTGGTGAT
              610       620       630       640

-V--D-----H-                             -S-----L-
          T  I  L  P  D  E  K  E  H  V  N  R  I
         CACAATCCTTCCGACGAAAAGGAACACGTTAATAGGATT
          || ||||||| ||||||||  |||||||  |||| |||
         TGTCGATCTACATGACGAAAAGGAGCATGTTAGCCGTCTA
              650       660       670       680
```

FIG 5F

```
     -S------N------T------K---T---L--L---
      C  S  R  D  R  P  G  E  T  A  D  R  N  M
     TGTTCAAGAGATAGACCGGGTGAAACGGCAGATAGAAATA
     ||||| |||| ||||  ||||| |||||  ||||| |||
     TCTTCACGGAATAGGACCGGCGAGAAAACAGATCTACTAA
            690       700       710       720

----------A---------------S--C---------
      L  R  T  L  N  A  V  V  Y  A  S  L  V  D
     TGCTCAGAACACTCAATGCCGTATACGGCATCTTTGGTGA
     ||||| ||  |||||||| || |||  |||||| || ||
     TGCTCAGGGCACTTAATGCAGTGTATTCCTGTTTAGTAGA
            730       740       750       760

-----I--M------H--I---------S----------
      T  V  K  Y  A  N  L  T  C  P  Y  E  K
     CACGGTTAAATACGCAAATCTAACATGCCCTTACGAGAAA
     ||| ||| ||||| ||||||| |||| ||||| || |||
     CACTATTATGTACGCAAATCATATTTGTCCCTACAGTAAG
            770       780       790       800
```

FIG. 5G

```
  D--E------S------D-----------D
  E  S  W  E  M  E  W  L  G  L  P  W  F  E
GAAAGCTGGGAAATGGAATGGTTGGACTTCCCTGTTTG
 ||  ||||||  ||||||||  ||||||||  |||||||
GATGAATGGAATCTGAATGGTTGGATCTACCATGGTTTG
        810           820           830           840

---------T-------A--T--T--------N--E---------T
           E  S  L  L  E  E  F  I  S  R  P  R  P
AAGAGTCATTACTTGAAGAATTCATCTCGCGCCCCGCCC
 ||||  ||  ||  ||  ||||  ||  ||  ||  |  ||
ATACATCTTTGCCACAACGTTTATAAACGAACCTCGTAC
        850           860           870           880

---...D--Y--R--G--S------V--S------H--H---------
     V  I  C  S  R  T  R  M  P  L  D  R  T
TGTTATTTGTTCGAGAACTCGAATGCCGCTGACCGAACT
 ||    ||||  ||  ||  ||||||  |||  ||  ||
TG...ATTATCGCGGTAGTAGGGTGTCATTACACCATACG
        890           900           910           920
```

FIG 5H

```
        |————————R————————|
 L  L  A  I  F  K  R  K  E  L  C  S  E  N
CTCCTGGCCATTTTTAAACGGAAAGAGCTGTGTAGCGAAA
 ||  ||  ||  ||||| |||   ||  |||  |  |  |
CTTTTAGGGATATTTAAGCGGGGAGAATTATGT
     930       940       950       960

G  E  L  L  T  Q  Y  S  W  I  L  W  G
ATGGGGAGCTGTTAACTCAGTATTCTTGGATATTGTGGGG
     970       980       990      1000

L  L  T  K  L  H  T  I  N  V  E  L  F
ATTACTGACTAAACTACACACCATTAATGTCGAATTATTT
    1010      1020      1030      1040

|————V——E——L——L
 D  I  S  G  M  S  R  R  E  C  A  S  A  I
GACATTAGCGGTATGTCACGTCGAGAATGGCCAGGCTA
                              ||  ||
                           TGTGTAGAACTGC
    1050      1060      1070      1080
```

FIG 51

```
     ---D----    ---S----   ---V---H--S---
     M H T M P E R L S T L A S
TAATGCATACTATGCCGGAGAGATTGTCTACTCTCGCTAG
|||  ||||||||  ||||||||||||  |||    |||
TTATGGATACTATGTCCGGAGAGATTGGTAACACATAGTAG
         1090       1100       1110      1120

------A---F----I----A-------L--A---
     W N D L C E L E D D V I S
CTGAATGATTTATGCCAGCTTGAAGATGATGTAATTTCC
||||||| |  ||||  |||||||||||| |||||||||
CTGAATGATGCCTTCGAGATTGAAGCTGATGTACTAGCC
    1130       1140       1150       1160

-----E------A--M--*-|
     Y N K G M C N E V G A S R *
TATAATAAGGAATGTGTAACGAGTTGGAGCGTCTCGAT
||||||||| |||||   ||||||
TATAATAAAGAGAATGGCTATGTAA
         1170       1180       1190      1200

AATTCTTCTTAATCTGCTGGTATTGGTTACTGCCATAACT
         1210       1220       1230      1240
```

FIG 5J

TATTATTGGTCCATGCCTAGAATAGTCATACGCTACGATCT
           1250          1260          1270          1280

GTTGCTATATATGACTATCGCCAAACTGTTAAACCCGCGA
           1290          1300          1310          1320

AGAATATATTTCATATAAACCTAAGGGCCCCTCAGTCTGA
           1330          1340          1350          1360

TTTTTGTGAAAACGTGTATACCA
           1370          1380

FIG 6A

1 CAGCTGCCTATGTAGTGAAATCTATACTGGATTT
ATCATAACTAGTTTACTTGTTGTATATTAGTAGCGCTATCT
TGACCAAATCGTTGTTCACATCTTGGCCATATACGTATTGATC

121 GTTGTTTCGAACCGCGAATAAAACTTTCATACATAC
TAAACGATGGAGTTGTGTTTTATGAGCGTTGAAAACAAAGT
ACCATCGGTTTAAAACTAAGTTGCATATCGTAATCCACAAAA

241 ATCATTTTATACATCATCCCGAAGAGACACCAAACG
                                M  L  T  P  R  V
TAACCCCTCTACATATCTTCCCTCATGCTCACGCCGCGTGT
L  R  A  L  G  W  T  G  L  F  F  L  L  L  S
TACGAGCTTTGGGGTGGACTGGACTCTTTTTTTTGCTTTTAT
                P  S  N  V  L  G  A  S  L  S  R
361 CTCCGAGCAACGTCCTAGGAGCCAGCCTTAGCCGG
D  L  E  T  P  P  F  L  S  F  D  P  S
GATCTCGAAACACCCCCATTTCTATCCTTTGATCCATCCA

FIG 6B

```
       N  I  S  I  N  G  A  P  L  T  E  V  P  H  A  P
    ACATTTCAATTAACGGGCGCCTTTAACTGAGTACCTCATGCAC
                            S  T  E  S  V  S  T  N  S  E  S  T
481 CTTCCACAGAAGTGTCAACAAATTCGGAAAGTACC

N  E  H  T  I  T  E  T  T  G  K  N  A  Y
    AATGAACATACCATAACAGAAACGACGGGCAAGAACGCATACA
    I  H  N  A  S  T  D  K  Q  N  A  N  D
    TCCACAACAATGCGTCTACGGACAAGCAAAATGCAACG
                                  T  H  K  T  P  N  I  L  C  D  T  E
601 ACACTCATAAAACGCCCAATATACTCTGCGATACGGA

E  V  F  V  F  L  N  E  T  G  R  F  V  C
    AGAAGTTTTGTTTTCCTTAACGAAACGGGAAGATTTGTTTGT
    T  L  K  V  D  P  P  S  D  S  E  W  S  N
    ACTCTCAAAGTCGACCCCCCTCGGATAGTGAATGGTCCA
                            F  V  L  D  L  I  F  N  P  I  E  Y
721 ACTTTGTTCTAGATCTGATCTTTAACCGAATTGAATA

H  A  N  E  K  N  V  E  A  A  R  I  A  G
    CCACGCCAACGAAAAGAATGTGGAAGCGGCGTATGCGTGGT
```

FIG 6C

```
      L  Y  G  V  P  G  S  D  Y  A  Y  P  R  Q
    CTCTATGGAGTCCCCGGATCAGACTATGCATACCCACGTC

S  E  L  I  S  S  I  R  R  D  P
841 AATCTGAATTAATTTCTTCGATTCGAGAGATCCCC

Q  G  T  F  W  T  S  P  S  P  H  G  N  K
    AGGGCACATTTTGGACGAGCCCATCACCTCATGGAAACAA

Y  F  I  W  I  N  K  T  T  N  T  M  G  V  E
    GTACTTCATATGGATAAACAACAACCAATACGATGGGCGTGG

I  R  N  V  D  Y  A  D  N  G  Y
961 AAATTAGAAATGTAGATTATGCTGATAATGGCTAC

M  Q  V  I  M  R  D  H  F  N  R  P  L
    ATGCAAGTCATTATGCGTGACCATTTTAATCGGCCTTTAA
    I  D  K  H  I  Y  I  R  V  C  Q  R  P  A  S  V
    TAGATAAACATATTTACATACGTGTGTGTCAACGACCTGCATCAG

D  V  L  A  P  P  V  L  S  G  E  N
1081 TGGATGTACTGGCCCCTCCAGTCCTCAGGGGAGAAAA

Y  K  A  S  C  I  V  R  H  F  Y  P  P  G
    TTACAAGGCATCTTGTATCGTTAGACACTTTTATCCCCCTGA
```

FIG 6D

```
       S  V  Y  V  S  W  R  Q  N  G  N  I  A  T
       TCTGTCTATGTATCTTGGAGACAGAATGAAACATTGCAA

P  R  K  D  R  D  G  S  F  W  W  F
1201   CTCCTCGGAAAGATCGCGATGGAAGTTTTGGTGGTT

E  S  G  R  G  A  T  L  V  S  T  I  T  L
       CGAATCTGGTAGAGGAGCTACGTTGTTTCTACAATAACATTG

G  N  S  G  I  D  F  P  P  K  I  S  C  L
       GGAAATTCAGGAATTGATTCCCCCAAAATATCTTGTC

V  A  N  K  Q  G  D  M  I  S  T  T
1321   TGGTTGCCTGGAAGCAGGGTGATATGATCAGCACGAC

N  A  T  A  I  P  T  V  Y  H  H  P  R  L
       GAATGCCACAGCTATCCCGACGGTATATCATCATCCCGTTTA

S  L  A  F  K  D  G  Y  A  I  C  T  I  E
       TCCCTCGCTTTTAAAGATGGGTATGCAATATGTACTATAG

C  V  P  S  E  I  T  V  R  W  L  V
1441   AATGTGTCCCCTCTGAGATTACTGTACGGTGGTTAGT

H  D  E  A  Q  P  N  T  T  Y  N  T  V  V
       ACATGATGAAGCCAGCCTAACACACAACTTATAATACTGTGTT
```

FIG 6E

```
         T  G  L  C  R  T  I  D  R  H  R  N  L  L
     ACAGGTCTCTGCCGACCATCGATCGCCATAGAAATCTCC

S  R  I  P  V  W  D  N  W  T  K  T
1561 TCAGCCGCATTCCAGTATGGACAATTGGACGAAAAC

K  Y  T  C  R  L  I  G  Y  P  F  D  E  D
     AAAATATACGTGCAGACTCATAGGCTACCCCTTCGATGAAGAT

K  F  Q  D  S  E  Y  Y  D  A  T  P  S  A
     AAATTCAAGATTCGGAATATTACGATGCAACTCCATCTG

R  G  T  P  M  V  I  T  V  T  A  V
1681 CAAGAGAACACCCATGGTTATTACGGTTACGGCAGT

L  G  L  A  V  I  L  G  M  G  I  I  M  T
     TTTGGGATTGGCTGTAATTTTAGGGATGGGATAATCATGACT

A  L  C  L  Y  N  S  T  R  K  N  I  R  L
     GCCCTATGTTTATACAACTCCACACGAAAAAATATTCGAT
                                       *
1801 TATAATCTCATTGTTATGTAGTGTGTGATTTATTAAAC

ATATTTTTTATAACTCTAGTATTCTCCGAGTACTTATATATT
```

FIG 6F

TATTTGTCAGACAATAATGCAATAGTCGAGAAACGTGAGG

1921 GGAGTCTCTGTAAACAGAATACGTATAATCATCTATTTG

AATAAAGATTGTCGTATAAATGAAGATAGCGCAAGTCATTC

CAAGCTCTCCATTCTATTTAAACAATGTACAGTTTAAAGT

FIG 7A

```
  1 GAATTCTTGTAAAATATCATTAATTCCGCTACCAACGGGTTCCTTTTTTCACATAGCTG
    F  E  Q  L  I  D  N  I  G  S  G  V  P  E  K  K  E  C  L  Q

61 CTGCTCCGTAGTTATCTTTTTTGCTGGAACCATTTCCCCAGGGAAGTACGGGTCATTCTC
    Q  E  T  T  I  K  A  P  V  M  E  G  P  F  Y  P  D  N  E

121 AGAAATGGTCCTAGCGGATCTCTTCCGAGGGTTATTCTCCGAGTATTCGCTATCCCGTTT
    S  I  T  R  A  S  R  K  R  P  N  N  E  S  Y  E  S  D  R  K

181 ATTATTTTTCTCAAGAGCCGAAATCAAGGCATCTAAGCGTGAAACAACAGTCTGCTCATG
    N  N  K  E  L  A  S  I  L  A  D  L  R  S  V  V  T  Q  E  H

241 TAATGATGGATACTGTATAGGATACGTTCCAGCCCCAGGAAACTGGCCGAAGTTCGAACT
    L  S  P  Y  Q  I  P  Y  T  G  A  G  P  F  Q  G  F  N  S  S

301 ATAATAATTTGGATGCACGGGGTAAGTAGATGCGGGCTTTGATAAGGAATATATGGGAA
    Y  Y  N  P  H  V  P  Y  T  S  A  P  S  Q  Y  P  I  Y  P  F

361 ACGCCCGCAGAAATTTGGGTCTTCGTAAAGAGCCGGTCTGTAAGTGTGGTTCATCCCCGG
    R  G  C  F  N  P  D  E  Y  L  A  P  R  Y  T  H  N  M  G  P
```

FIG 7B

```
421 ACCCATAAAAGATTCTAGGCGAGGGTGTCGTTCGAATCCACGCGGCCAAATATCACGTCC
     G  M  F  S  E  L  R  P  H  R  E  F  G  R  P  W  I  D  R  G

481 TGGTGAACATTCGTGAGTAGAGTCCCGCGACCTACGGGAAAACTCTCGTGATGGCGACAC
     P  S  C  E  H  T  S  D  R  S  R  R  S  F  E  R  S  P  S  V

541 GGGTCTCCGGTCGTTATCTCTGCGGCTGATGCCCAAGAAGACTCGCATACTTCTCGAA
     P  R  R  D  N  D  R  R  A  S  A  A  L  L  S  A  Y  K  E  F

601 TGGGACATAGACCATATCTTCACGAGATGCGGACGGTGAAGCTCCGTTTTTGTTTGCAA
     P  V  Y  V  M  D  E  R  S  A  S  P  S  A  G  N  K  T  Q  L

661 GAACTGGCCGGAGCATGTCGCCCGACTCCATGGCTGGGCCGTTTGCGTAGAAACTGAACGGTGTTTGCCCGACGGTTG
     F  Q  G  S  C  T  A  S  E  M  A  P  V  H  T  Q  G  S  P  Q

721 CTGACTCTCGCTTATATCGAAGCTTCCGGAGTCTTCCTTAATCCCTATGGTTATTACCTCATTCGC
     Q  S  E  S  I  D  F  S  P  A  T  Q  T  S  V  S  R  D  K  I

781 AGCATTCTCAGGAGTCTTCTTCGGAGTGTTCCTTAATCCCTATGGTTATTACCTCATTCGC
     A  N  E  P  T  E  E  S  H  E  K  I  G  I  T  I  V  E  N  A

841 TTGTAAATATTTCGGGTTGTAAACAGCTGCCATCTCCGCGTTTCAAACAGGTACC
     Q  L  Y  K  P  N  Y  A  A  M  E  R  R  T  K  L  C  T  G

901 CCTATCCATCAAAAACGCCCCGTGAATAAATTTCTTCATCAGGACTCGCGTAATTCTGG
     R  D  M  L  F  A  G  H  I  F  K  K  M  L  V  R  T  I  E  P
```

FIG 7C

```
 961  TCGCGACAACTCTCTAGGGACTTCTGCACATTTCTTCACGTGTAGCTATTTCATACAGCTG
        R  S  L  E  R  P  V  E  A  C  K  E  R  T  A  I  E  Y  L  Q

1021  TTCTTTAATTGGTGCGCTCAAATCATCAAATGCTCCAATAGCTTCCGAAGCGGTGGCCCC
        E  K  I  P  A  S  L  D  D  F  A  G  I  A  E  S  A  T  A  G

1081  GTAAATTGCTACCGTGCCTTCACGTCTACCCAACTCACAGAGCGCCACGTGTGCAAAAAA
        Y  I  A  V  T  G  E  R  R  G  L  E  C  L  A  V  H  A  F  F

1141  ATCTTTTCCGGGCACTTCGTTCTCTTTTCAAGCCCTTGAAGAGAGCGATAGAGAAGGTAG
        D  K  G  P  V  E  N  K  E  L  R  R  S  S  L  S  P  L

1201  AATGTTGCTGAGAAGATAGAGAAATTTCTCTGTCTCCGTCAAAACCATCCCCTCTTCGGC
        I  N  S  L  L  Y  L  F  K  E  T  E  T  L  V  M  G  E  E  A

1261  ATTCGCAAAAGAGCATCATCTTGCACGTAGCTTAAAAAAATAGGTGCAAGAGCAGTTGA
        N  A  F  L  A  D  D  Q  V  S  L  F  I  P  A  L  A  T  S

1321  CACGACACCCAAACAAAACAGTCCCTCCGGCAGGTCTAAGATCGTCAGCACTGTACCTAC
        V  V  G  L  C  F  L  G  R  P  L  D  L  I  T  L  V  T  G  V

1381  CACGCAGGATGACTCGTGGTCAATGTTTATCGGAATTGTTCCAGGCAAAACTGGTAAAGC
        V  C  S  S  E  H  D  N  I  P  I  T  G  P  L  V  P  L  A

1441  CGATTTGCTTTGCTCGCGAGTAAGCTCATATTCTCGCCCGGCACTTTCTTGGTGGTCATA
        S  K  S  Q  E  R  T  L  E  Y  E  R  G  A  S  E  Q  H  D  Y
```

FIG 7D

```
1501  TACTACCAAATAGCCCGGCAACGAAGATATATTTGATGTCGACGTTCTCCGACATAGCGAG
         V  V  L  Y  G  A  V  F  I  Y  K  I  D  V  N  E  S  M  <<ORF1

1561  ACCGACTCGACCCGCAAAGTATCAACACACTGACAAAACAGACGGACTGATCAGAAAGAT

1621  ATAACCCTTTTATTGTCTAAACAGAGACGCGATCGCGAAATACTAAGCATTATCCATAT

1681  GTCACGTGATGTGGCAAGCATCCAAGACACATAAAATAGATCAGGTCAGAATCAGACTCC
                                                           *  V  G

1741  ACGTTGAATGTCCTCAATATTCCTTTCAAATGCTTTTTTTGCATCAAATACCTCAAGTAA
         R  Q  I  D  E  I  N  R  E  F  A  K  K  A  D  F  V  E  L  L

1801  CCTGGACACTCCCTCTTCAACGTCACCTGTCAATGAATCGTGTACCGCCAAAACAGCAGC
         R  S  V  G  E  E  V  D  G  T  L  S  D  H  V  A  L  V  A  A

1861  TGCCCCGCTACCCACATGTGACGTTTTTCTGAGATCAAGCTCAATTAGATTACAGAGGGA
         A  G  S  G  V  H  S  T  K  R  L  D  L  E  I  L  N  C  L  S

1921  GGAATAGTACTCCCCAACCGTACCGTCGGTATTCCTTTAACGCGCCCCGTTATGCA
         S  Y  Y  E  G  L  R  V  A  T  P  I  G  K  V  R  G  T  I  C

1981  GAGTGCAGCTAAACCAGGAAAGAAGAACCAGTAACTTCACATCTGTTGTCATATCTATACAT
         L  A  A  L  G  P  F  F  G  T  V  E  C  R  N  D  Y  R  Y  M
```

FIG 7E

```
2041 AGGTACAACATATTTCTCGAATAAAAGAACAAGTTGTGTCGCGACTGGCCATATCTTG
      P  V  V  Y  K  E  F  F  L  N  N  D  R  S  A  M  D  Q

2101 TCCATTGTCATCAAATGTGCTTGCGGTGCCTTGAGGTCTTGCCAGGGGCGACGGGCCA
      G  N  D  F  T  S  A  T  A  Q  P  R  S  G  P  A  V  P  W

2161 TTTAGCTGCCTCCTGTTCCGATTGGGTTCCAAGTGGCAATTCAAAGAACGCAGATGGCTG
      K  A  A  E  Q  E  S  Q  T  G  L  P  L  E  F  F  A  S  P  Q

2221 AAATCGATTGAGATGTGTGCTCGTATAGACATTACTATTAAACATTAGCTTTTGCAAGAC
      F  R  N  L  H  T  S  T  Y  V  N  S  N  F  M  L  K  Q  L  V

2281 TAGGAGCAGAGATATCGAGTCTATAACCGTTCGCACAAGCGGATCATCTTCATGAAGAAT
      L  L  L  S  I  S  D  I  V  T  R  V  L  P  D  D  E  H  L  I

2341 TAACGGCGTTCGTCTCGAAGGGAAAAATGAAGCAGAGTTTCTTTCGTTATATCTCGTACTGTGGT
      L  P  T  R  R  S  P  F  F  S  I  S  L  A  A  I  P  D  D  F

2401 ACGAACAAAATCTGGATCTATTGGAAGCTTTAGCAATTGATACACTATGTGAGGATCGAACACTCCATT
      R  V  F  D  P  D  I  P  L  L  T  E  K  T  I  D  R  V  T  T

2461 GGAAAGGGTCCCAGTACGCTTTAGCAATTGGGAAAAAAGTTTACGGGAGTTTGACCGGTCAAT
      S  L  T  G  T  R  K  L  Q  Y  V  I  H  P  D  F  V  G  N

2521 CGAATATTTCTGCCGTCAATTGGGGAAAAAAGTTTACGGGAGTTTGACCGGTCAAA
      S  Y  K  R  G  D  I  P  S  F  F  N  V  P  L  K  S  R  D  F
```

FIG 7F

```
2581 TGAAAATGTAACTGAGCCCCACTCGGCCCCGAATATCTTCCAGCATATAATTTAAATACGT
      S  F  T  V  S  G  W  E  A  R  I  D  E  L  M  Y  N  L  Y  T

2641 TGGAACATGTCTTAATGCATCTTCAAATATAGAAACATCAAGACCATGTCTAATGTTTGA
      P  V  H  R  L  A  D  E  F  I  S  V  D  L  G  H  R  I  N  S

2701 AGCAGATTGTCTAGACCGGAGTAGTGCAGTAAGCATAAACAGTAGCCTCGAATCCGCT
      A  S  Q  R  S  R  S  Y  H  L  L  C  L  V  T  A  E  F  G  S

2761 ATATTGTCGAGTCCCCAGCATAAATTTCCATCGCCGATCGCAGCGCTCGAATAGCCGTTT
      Y  Q  R  T  G  A  Y  I  E  M  A  S  R  L  A  R  I  A  T  K

2821 CATAAACCGCCCCGAGATGCGCGTGTCTCCCATTACATTCAAAACCCTAGCGATAGCTTT
      M  F  R  G  S  I  R  T  D  G  M  V  N  L  V  R  A  I  A  K

2881 ATTGTTATCTAGGAGCTGAGTCTGTAGCGCGGAACCAAGACCCGAATCCCAGCCGGCC
      N  D  L  L  Q  T  Q  L  A  R  F  W  S  G  F  G  L  R  G

2941 ATTGCCAGCAATAGCAAACGAAGTTGTCAGAAAATCTACTTGAAAATCTGTATTAAAAGT
      N  G  A  I  A  F  S  T  T  L  F  D  V  Q  F  D  T  N  F  T

3001 TAATGGTTCTCCATTCTTAACTATCCAAATTACGTTCGCAGGACATCCTCGCCAGGCGC
      L  P  E  G  N  K  V  I  W  I  V  N  A  P  V  D  E  G  P  A

3061 ACGGATGTCTAGTGTTTATAAGACCCAACAATGTCCTTCTCCTGCACGGCCCGCTGGGC
      R  I  D  L  T  K  Y  S  G  V  I  D  K  E  Q  V  A  R  Q  A
```

FIG 7G

```
3121 TAAATCATCCAAGACATCAATTACAGTCTCTAGGGATATTCAATAGTTTGCAATGCCGA
     L  D  D  L  V  D  I  V  T  E  L  P  Y  E  I  T  Q  L  A  S

3181 TGAGACATGTACGGGAACAGTAGCGCTCCAGTTGCTCTAAAGCTGCCTTGGC
     S  V  H  P  V  T  A  S  M  N  E  L  Q  E  L  A  A  K  A

3241 AGCCCTGTTCCGCCTTTCCAGATCTTCAATCCTTGCACGATTGGTCATGATTTCTGCGTC
     A  R  N  R  R  E  L  D  E  I  R  A  R  N  T  M  I  E  A  D

3301 TATTAGAGTTCCTTCGAAAAGCTTAGATGCATATTTACTCGAGCCTTCCGCCAGGAGAT
     I  L  T  G  E  F  L  K  S  A  Y  K  S  S  G  E  A  C  S  I

3361 AAAGTTTAAACGATCGGCTAAAACCATCAAGGTAGACGGCTTGTTGCTCCTTTGGTAA
     F  N  L  R  D  A  L  V  M  L  T  S  P  K  N  S  D  K  P  L

3421 ATTCATAGGTTCGAATCTGGGTCGAAACATGGTTCGGACAAGTTTTTGGACTCCTCCGTA
     N  M  P  E  F  R  P  R  F  M  <<ORF 2
     *  L  N  S  D  P  P  D  F  C  P  E  S  L  N  K  S  E  E  T  S

3481 GAAGTGGAATAGCTCGCGGGTTTGGTTGCGGACTCTTTTCCACGCCGACGAAAACAAT
                       T  S  Y  S  A  P  K  T  A  S  E  K  G  V  R  S  S  F  L  A

3541 GCAGCTACGGTTTGTAAGGCTGAAGGGCCTAGATCCGCATTCTTTGCACTT
                       A  V  T  Q  L  A  S  P  A  P  S  A  L  D  A  N  K  A  S  E
```

FIG 7H

```
3601 TCTTGTTGATACTTACTGCGCGCATGCGACACGGCTGGCTCTCTAATTTCGCGCAGAAAGTC
      Q  Q  Y  K  S  R  A  H  S  V  R  P  E  L  K  A  C  F  T  K

3661 TTTAAATACTGGCTTCTGGTAGCTAGAGTGACAAAGAAAAGCTCAGACGATACATTTATA
      L  Y  Q  S  R  T  A  L  T  V  F  F  L  E  S  S  V  N  I  V

3721 ACCGTTTCCCCAACCGTTTTTACCGCCAAGATGTTCATCCCCCCGTTGAGCAACAAATACC
      T  E  G  V  T  K  V  A  L  I  N  M  G  R  Q  A  V  F  V  L

3781 AGTAGAGAAAGAATCTTTACTTTCTCAGTGCCAGTATATCCTTGTCTTAATTTACTTTCAGTCATC
      L  S  L  I  K  V  K  E  T  G  P  V  A  L  N  E  L  L  R  A

3841 GCAGAATCGCGAAGTTGGAGAGTGCCAGTATATCCTTGTCTTAATTTACTTTCAGTCATC
      S  D  R  L  Q  L  T  G  T  Y  G  Q  R  L  K  S  E  T  M  L

3901 AAAGATTTGGAAAAACAACGACACATGTTTTCAATCACAATACATTTCATTTCATGTTGT
      S  K  S  F  R  C  T  K  L  E  I  V  I  C  K  M  E  H  Q  T

3961 GTCTCCAGCAAACAATGCAATCAGGTTTCCGCAACCCTAGGTTCACTTCAAACATGACT
      E  L  L  C  I  C  D  P  K  R  L  G  L  N  V  E  F  M  V  V

4021 ACAATTTTGCCCCGGCCAGGTTTGCATTGGGGAATTATCGTATAGGCCAGCCTTCCGTCT
      I  K  G  G  A  P  K  C  Q  P  I  I  T  Y  A  L  R  G  D  G

4081 CCACCCCCTTCAAAGACTTCCTCCAGTGATCTGACGAGAGCTCGGTAAAAGGATTATGG
      G  G  E  F  V  E  E  L  S  R  V  L  A  R  Y  F  R  N  H  C
```

FIG 71

```
                          ORF 4 >>  M   A   V   A   G   A   V   K   T
4141 CAACGGATTCCGGCATTTAGTCTAGCCCCGCAGAGATGGCCGTAGCTGGCGCCGTGAAAAC
      R   I   G   A   N   L   R   A   R   L   S   P   R   L   Q   R   R   S   F   K
      S   G   G   V   Q   F   C   S   E   F   E   N   D   D   S   D   F   R   R   V
4201 TTCCGGTGGTGTGCAGTTTTGCTCCGAGTTCGAGAACGATGACTCCGACTTTCGCCGCGT
      R   H   H   A   T   K   S   R   T   R   S   R   H   S   R   S   E   G   R   Q
      V   L   L   Y   V   D   G   P   F   G   V   G   K   T   V   A   K   T   L
4261 TGTACTTCTTTACGTCGACGGGCCATTCGGAGTCGGTAAAACAGTCACTGCAAAGACGTT
      V   E   K   R   R   R   A   M  <<ORF 3
      M   Q   M   P   N   W   R   G   C   R   L   Y   L   A   E   P   M   Q   A   W
4321 GATGCAAATGCCAAATTGGAGAGGTTGCCGTCTATACTTAGCGGAACCTATGCAAGCATG
      R   Q   W   F   G   G   A   D   M   I   K   E   I   N   E   I   Q   T   L   K
4381 GCGCCAATGGTTTGGCGGGGAGCCGGATATGATCAAAGAAATTAATGAAATACAAACCCTAAA
      A   S   G   K   L   E   C   R   E   A   S   P   V   A   V   A   E   V   Q   M
4441 GGCTTCCGGAAAACTTGAATGTCGGGAGGCGTCTCCGGTTGCCGTAGCGGAAGTTCAGAT
      T   I   A   A   P   L   R   I   M   N   H   V   I   Y   N   Y   L   G   S   E
4501 GACTATTGCTGCCCCACTAAGAATAATGAACCACGTCATTTATAATTATTTGGGATCTGA
      R   C   Y   S   A   A   A   S   G   P   D   D   V   L   F   L   V   D   R   H
4561 ACGCTGCTACAGCGCAGCTGCATCCGGACCAGATGATGTCTTATTCCTCGTAGATAGGCA
```

FIG 7J

```
                P   L   A   A   C   L   F   P   V   A   Q   Y   L   S   G   A   L   E   F
4621  CCCACTCGCGCGGCATGTTTGTGTTTCCCTGTTGCACAATATCTAAGCGGAGCCGCTCGAATT

G   D   L   I   T   L   L   S   G   I   P   D   I   P   T   H   S   N   I   V
4681  TGGAGAGATTTAATAACTTTATTGTCAGGAATTCCTGACATTCCAACACACTCCAACATTGT

L   M   D   L   D   I   C   E   Q   A   R   R   I   I   Q   R   G   R   P   G
4741  TTTAATGGATTTGGATATTTGCGAACAGGCACGGCGTATAATACAAAGGGGGCGCCCAGG

E   T   V   D   W   T   Y   L   C   A   L   R   N   S   Y   I   C   L   M   N
4801  GGAAACGGTCGACTGGACGTATTTGTGTGCATTACGTAACTCGTACATCTGCCTCATGAA

T   T   T   Y   L   Q   R   T   S   Y   P   A   L   L   K   E   Q   E   A   L
4861  TACTACCACCTACCTCCAACGTACATCTTATCCAGCATTGTTGAAGGAGCAAGAAGCCTT

T   S   A   T   L   L   K   F   K   R   E   C   L   E   T   A   T   V   P   E
4921  AACAAGTGCCACGCTCTTAAAATTCAAGAGAGTGCTTAGAAACTGCTACTGTTCCAGA

I   N   P   S   I   D   Q   T   L   F   A   I   L   A   F   D   Q   Q   N   V
4981  AATCAATCCTTCAATCGACCAGACGCTATTTGCAATATTAGCTTTTGATCAGCAAAATGT

H   G   E   R   L   K   T   V   L   S   F   V   V   Q   K   L   A   T   V   L
5041  TCACGGGGAAAGATTAAAAACTGTACTTTCATTTGTGGTTCAAAAACTCGGACGGTATT

K   N   L   C   I   F   Y   L   P   A   H   G   L   T   P   E   A   C   A   L
5101  GAAAAACTTGTGCATTTTTTACTTACCAGCACATGGCCTCACCCCGGAGGCATGTGCACT
```

FIG 7K

```
       K   C   L   E   F   A   E   T   A   S   S   L   T   T   K   R   A   A   I   A
5161   GAAATGTTTAGAGTTTGCCGAGACGGCAAGTTCTCTTACAACCAAACGAGCGGCGATCGC

S   L   I   D   A   V   E   R   Y   N   A   D   M   G   S   *
5221   GAGCTTAATTGACCGCAGTAGAGCGCTACAATGCTGATATGGGTTCGTAATGTTCCGCTTC

M   S   F   T   H   F   L   A   L   Y   S   F   L
5281   CATAATCCTTCACAATAAGAGTATGTCCTTTACTCATTTCCTTGCTTTGTACTCATTCTT

L   E   R   A   W   L   H   Q   Q   P   A   P   M   G   H   A   R   E   I   F
5341   ACTCGAGAGAGCGTGGCTTCACCAGCAACCCGGCCGATGGGACACGCCGAGAGAAATATT
```

Figure 9 ILTV gB

```
  V   L   I   S   N   W   R   Q   C   C   R   R   A   Q   P   R   H   C   H   R
CGTGCTAATCTCCAATTGGCGCCAGTGTTGCAGGCCCAGCCACGACATTGTCACCG
           10          20          30          40          50          60

H   A   E   S   T   N   M   T   E   G   R   A   V   V   F   K   Q   N   I   A
ACATGCCGAGTCGACTAACATGACTGAAGGAAGGGCCGTAGTCTTCAAGCAAAACATTGC
           70          80          90         100         110         120

P   Y   F   N   V   T   L   Y   Y   K   H   I   T   T   V   S
CCCGTACGTCTTTAATGTGACTCTCTATACTATAAACATATAACCACAGTTAG
          130         140         150         160         170
```

Figure 10 ILTV Ribonucleotide reductase.

HVT HOMOLOGUES OF VZV62/ HSV-1 IE 175

```
  S   N   V   V   R   Y   M   C   G   N   T   V   L
TCGAATGTGGTGCGATACATGTGCGGGAACACGGTACTCC
         10          20          30         40

P   P   D   P   H   G   T   P   V   V   I   N   V   P
CCCCCGGATCCCCATGGCACCCCGTGGTGATCAACGTTCC
         50          60          70         80

E   G   T   S   E   T   M   A   E   L   T   V   A
CGAGGGAACGTCCGAAACTATGGCGGAGCTTACTGTTGCT
         90         100         110        120

H   V   G   R   K   S   I   G   W   P   T   S   E
CACGTTGGGCGCAAGTCTATTGGGTGGCCGACCTCCGAGT
        130         140         150        160

W   H   S   A   T   I   L   Q   K   D   N   D   S   R   L   V   I   I   R
GGCATTCCGCTACAATCCCTGCAGAAAGATAATGATAGTCGGCTGGTAATTATACGCC
        170         180         190         200        210
```

FIG 12

HVT HOMOLOGUE OF RIBONUCLEOTIDE REDUCTASE (LARGE SUBUNIT)

```
  Q  V  T  E  V  S  E  G  F  A  P  L  F
 CAAGTGACCGAGGTTAGCGAAGGATTTGCCCCTTTGTTCA
         10        20        30        40

S  N  M  F  S  K  V  T  S  A  G  E  L  L
GTAACATGTTCAGCAAGGTGACAAGTGCCGGGAACTGCT
        50        60        70        80

R  P  N  S  Q  L  M  R  E  L  R  Q  I
TAGACCCAACAGTCAATTAATGCGGGAGCTGAGACAAATA
        90       100       110       120

Y  P  D  N
TATCCCGATAAT
        130
```

FIG. 13A

MDV HOMOLOGUE OF RIBONUCLEOTIDE REDUCTASE ( LARGE SUB-UNIT )

```
  N   S   Y   Y   A   R   G   R   L   H   F   D   G
TAACAGTTATTATGCACGAGGACGTCTGCATTTCGATGGG
         250           260           270        280
  W   A   N   V   E   L   A   A   V   E   E   W   N
TGGCTAATGTAGAATTGGCTGCAGTGGAAGAGTGGAATA
         290           300           310        320
```

FIG 14

MDV HOMOLOGUE OF RIBONUCLEOTIDE REDUCTASE (SMALL SUB-UNIT)

MDV HOMOLOGUE OF HSV-1 IE-175

```
  P   I   P   Y   V   E   E   M   K   D   Y   A
CCCATTCCCGTCTATGTAGAGGAAATGAAAGATTATGCCA
         10        20        30        40

MDV HOMOLOGUE OF HSV-1 IE-68

```
         S   D   Q   D   F   E   L   N   N   V   G   K   F
        CGTCCGATCAAGACTTTGAACTTAATAATGTGGGCAAATT
                 10        20        30        40

C   P   L   P   W   K   P   D   V   A   R   L   C
        TTGTCCTCTACCATGGAAACCCGATGTCGCTCGGTTATGT
                 50        60        70        80

A   D   T   N   K   L   F   R   C   F   I   R   C   R
        GCGGATACAAACAAACTATTTCGATGTTTTATTCGATGTC
                 90       100       110       120

L   N   S   G   P   F   H   D   A   L   R   R   A
        GACTAAATAGCGGTCCGTTCCACGATGCTCTTCGGAGAGC
                130       140       150       160

L   F   D   I   H   M   I   G   R   M   G   Y   R   L   N
        ACTATTCGATATTCATATGATTGGTCGAATGGGATATCGACTAAA
                170       180       190       200
```

VIRAL NUCLEOTIDE SEQUENCES

This is a division of application Ser. No. 08/125,039 filed Sep. 22, 1993 which in turn is a continuation application of Ser. No. 07/669,391, filed Apr. 29, 1991, abandoned, which is a 371 of PCT/6B89/01075 filed Sep. 13, 1989.

The present invention relates to viral nucleotide sequences which may be manipulated to provide vaccines against disease.

BACKGROUND AND DESCRIPTION OF PRIOR ART

Herpesviruses are large double stranded DNA viruses consisting of an icosahedral capsid surrounded by an envelope. The group has been classified as alpha, beta and gammaherpesviruses on the basis of genome structure and biological properties [Roizman, B et al (1981) Inter-virology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis-Virus (ILTV) (an alphaherpesvirus) which causes an acute upper respiratory tract infection in chickens resulting in mortality and loss of egg production.

A recent unexpected finding in out laboratory is that there is sufficient amino acid homology between MDV, ILTV and mammalian herpesviruses, particularly varicella zoster (VZV) and Herpes Simplex Virus (HSV) to allow identification of numerous conserved genes. These include the MDV and Herpesvirus of Turkeys (HVT) homologues of glycoproteins gB, gC and gH of HSV; the ILTV, MDV and HVT homologues of TK and ribonucleotide reductase genes and the ILTV homologue of gB and genes 34 and 35 of VZV [Buckmaster, A et al, (1988) J. gen. Virol, 69, 2033–2042.

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic.. These observations and the fact that there are MDV type-specific epitopes that are not shared by HVT or type 2 MDV have led us to the conclusion that improved vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 13–31, Macmillan, 1986].

Infectious laryngotracheitis is also a worldwide problem. Sporadic outbreaks occur in which the severity of clinical symptoms varies considerably. Virus can persist in birds that have recovered and may be shed at intermittent intervals after recovery. An attenuated field strain is currently used as a vaccine. However, it has retained some degree of pathogenicity. Mortality due to the vaccine may reach 10% in young chicks.

A number of herpesvirus antigens have been shown to confer protective immunity when expressed in a recombinant vaccinia virus. These include the gB gene of HSV [Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpes-viruses, gB and its homologues are important immunogens. Moreover, the presence of gB at the surface of infected cells has been shown to be an important target for humoral and cell-mediated immune responses [Blacklaws, B. A. et al J. gen. Virol. 68, 1103–1114 (1987); McLaughlin-Taylor, E. et al (1988) J. gen. Virol. 69, 1731–1734]. The recently described glycoprotein gH of HSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV eShih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TK- virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragement of HSV TK and the recombinant was introduced into the PRV mutant by homologous recombination. TK- virus was selected which expressed the human gene (Thomsen et al as above). Similarly, VZV has been used as a vector [Lowe et al (1987) Proc. Natl. Acad. Sci. U.S.A. 84, 3896–3900].

Several herpesvirus genes have also been shown to be associated with virulence and to be non-essential for growth in vitro. These include the TK genes of HSV [Jamieson, A. T. et al (1974) J. gen. Virol. 24, 465–480; Field, H. and Wildy, P., (1987) J. Hygiene (Cambridge) 81, 267–277] and of PRV. Indeed it has long been known that PRV is readily attenuated by deletion of TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity [Rosen, A. et al (1986) Virus Research 5, 157–175; Thompson, R. L. et al (1983) Virology 131, 180–192]. Several additional genes of HSV have been shown to be non-essential for growth in vitro although it is not known whether they are associated with virulence. These include UL24 (Sanders, P. G., (1982), J. gen. Virol. 63, 277–295, large subunit of ribonucleotide reductase (Goldstein D. J. and Weller, S. K. (1988) J. Virol. 62, 196–205), gC (Draper K. G. et al (1984) J. Virol. 51, 578–585), dUTPase (Fisher, F. B. & Preston, V. G. (1986) Virology 148, 190–197), and $U_L55$ and $U_L$ 56 (MacLean, A. R. & Brown, S. M. (1987) J. gen. Virol. 68, 1339–1350).

Moreover there is evidence that several genes of HSV mapping in Us are also non-essential for growth in vitro [Weber, P. C. et al (1987) Science 236, 576–579].

SUMMARY OF THE INVENTION

One aspect of the present invention provides a nucleotide sequence substantially free of the sequences which would adjoin it in the wild-type virus associated with the sequence, the sequence being selected from the group consisting of:

(a) the HVT homologue of the HSV gB gene, (b) the HVT homologue of the HSV gC gene, (c) the HVT homologue of the HSV gH gene, (d) the TK gene of ILTV, (e) the ILTV homologue of the HSV gB gene, (f) ORF2 of ILTV, (g) ORF3 of ILTV, (h) the ribonucleotide reductase (large subunit) gene of ILTV, (i) the ribonucleotide reductase (large subunit) gene of HVT, (j) the ribonucleotide reductase (small subunit) gene of MDV, (k) the ribonucleotide reductase (large subunit) gene of MDV, (l) the HVT homologue of the immediate early gene IE-175 of HSV-I, and (m) the HVT homologue of the immediate early gene IE-68 of HSV-I, and minor variations thereof.

Each of sequences (a) to (m) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (l) and (m) above.

The term "minor variations thereof" is intended to include changes in the nucleotide sequence which do not affect its essential nature, for example minor substitutions of nucleotides for one another. In the case of sequences which are intended for insertion into a vector to encode an antigen, the "essential nature" of the sequence refers to the (glyco) protein encoded. Conservative changes in the nucleotide sequence which give rise to the same antigen will clearly be included, as will changes which cause conservative alterations in the amino acid sequence which do not affect adversely the antigenic nature of the antigen, in particular, antigenic portions of the antigen sequences may be used alone, for example the regions corresponding to nucleotides 273–320 or 867–926 of HVT gH and minor variations thereof. These sequences and the peptides encoded thereby form a further aspect of the invention. In the case of a sequence which is an insertion site, it is necessary only that the sequence should be non-essential for the infectivity and replication of the virus and have sufficient homology with the defined sequence to enable recombination to occur. Thus an insertion of one nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous.

It will be appreciated that such degrees of homology relate to substantially the entire portion of each sequence (a) to (m) defined above. Shorter sequences may be used as probes in the identification or isolation of such longer sequences, but in this case the degree of homology will in general need to be greater in order to ensure accurate hybridisation.

Thus, a further aspect of the invention provides subsequences of at least 13 nucleotides having at least 90% (preferably 95%, 99% or 100%) homology with at least one portion of any of the said sequences (a) to (m) above.

In the above list, sequences (a) to (c), (e), (f), (l) and (m) are useful for expressing viral antigens. Sequences (b), (d) and (g) to (k) and, in addition, the TK region of MDV are useful as non-essential sites suitable for insertion of antigen-expressing genes. Thus, sequence (b) is useful for both functions.

The sequences may readily be isolated from naturally-occurring ILTV, HVT and MDV viruses, using the sequence information given herein and standard techniques, for example involving the preparation of oligonucleotide probes and use thereof to hybridise to the naturally-occurring DNA.

Antigenic ILTV and HVT sequences, i.e. sequences (a) to (c), (e), (f), (l) and (m) above, may be expressed in any suitable host and, in particular, in HVT or MDV. Suitable non-essential sites for insertion of one ILTV sequence include the MDV homologue of the HSV gC gene, the HVT homologue of the HSV gC gene, the TK gene of HVT or MDV, the ribonucleotide reductase (large subunit) gene of HVT or MDV and the ribonucleotide reductase (small subunit) gene of MDV.

A second aspect of the invention provides insertional or deletional mutants of MDV, HVT and ILTV as follows:

(i) for HVT, a mutation in the region homologous to the RSV gC gene or in the ribonucleotide reductase gene. or the TK gene, (ii) for MDV, a mutation in the region homologous to the HSV gC gene or in the ribonucleotide reductase (small subunit) gene or in the ribonucleotide reductase (large subunit) gene, (iii) for ILTV, a mutation in the TK gene, ORF3 or the ribonucleotide reductase (large subunit) gene.

Each mutation may be in the coding or non-coding sequences of the regions identified.

Such mutant forms of HVT, MDV and ILTV may be used as, or created in the course of preparing, viral vectors for heterologous antigen-encoding sequences, or indeed as vectors for any other sequence which one wishes to express in a fowl in which the vector will replicate. Such sequences include, but are not limited to, (a) to (c), (e), (f), (l) and (m).

By "heterologous", we mean that the antigen-expressing sequence has not previously been found in the same place in relation to the remainder of the viral genome. For example, an antigen-expressing gene might be isolated from a virulent strain of ILTV and inserted into the TK region of a less virulent strain of ILTV; this insertion would be regarded as "heterologous" if it did not result in a naturally-occurring virus.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursal disease (Gumboro), inclusion body hepatitis (adenovirus), lymphoproliferative disease of turkeys, Newcastle disease, reticuloendotheliosis in chickens, reticulo-endotheliosis in turkeys, rotavirus enteritis, turkey haemorrhagic enteritis and turkey rhinotracheitis. The sequence may alternatively encode paramyosin (a muscle protein common to all invertebrate parasites) or an antigenic part thereof, somatostatin or a growth-promoting part thereof or an immune regulator.

The vectors in accordance with the invention may provide multivalent vaccine protection. For example, a vaccine comprising ILTV carrying an MDV antigen coding sequence would be expected to protect against ILT and Marek's Disease.

Furthermore, the mutant ILTV viruses themselves are potentially useful in vaccines as attenuated viruses, without necessarily having a heterologous sequence inserted.

A convenient process for preparing the deletional or insertional mutants of the second aspect of the invention comprises simply introducing into a suitable cell, for example by co-transfection, a deletional or insertional mutant version of the appropriate region (for example, the TK region) and either whole viral DNA or a whole virus (for example the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells and duck embryo fibroblasts, all preferably grown in sub-confluent monolayers in Petri dishes.

The transfected DNA and the whole viral DNA will then recombine with one another in the infected cells by homologous recombination and the desired recombinants can be screened for, for example by the detection of hybridisation to suitable probes or by an immunoassay using suitable antibodies to the gene product of the region in question.

For homologous recombination to take place, the viral DNA must replicate. At present, no cell-free replication system for MDV, HVT or ILTV is known. However, if such a system becomes available, then the process of the invention could be operated therein. The environment in which the replication and recombination occur is not critical.

The ILTV and HVT regions which were identified above as being responsible for encoding immunologically useful viral antigens can be inserted into suitable vectors, for example into HVT or into other vectors such as fowlpoxvirus, bacteria or fungi. In the case of viral vectors, especially herpesvirus vectors and poxvirus vectors, such insertion can be achieved by recombination betwen the antigen-encoding sequence, flanked by suitable non-essential sequences, and the vector's genome in a suitable host cell as described above. A promoter which is endogenous to the host will usually be used to control expression of the heterologous (viral antigen-encoding) sequence. In the case of bacteria and fungi, the antigen-encoding sequence may be inserted using known or yet-to-be-discovered techniques of DNA manipulation. A non-pathogenic strain of Salmonella may be used as such a host. The heterologous sequence may be inserted into the host's genome or be carried on an independently-replicating plasmid.

The flanking sequences which are used may comprise all, virtually all or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, the construction of deletional or insertional mutants of ILTV can yield improved vaccines. Alternatively, the expression of ILTV glycoproteins or other ILTV proteins engineered into HVT, fowl pox or other vectors can constitute effective vaccines.

To prepare a vaccine in which HVT, MDV or ILTV is the virus or vector, the virus is grown in suitable cells such as chick embryo fibroblasts in a standard culture medium which as 199 medium (Wellcome or Flow Laboratories) for 3 to 4 days at about 37° C. The cells are harvested by scraping from the surface of the culture or by trypsinisation and suspended in medium containing 1 mM EDTA or 10% dimethyl sulphoxide and in either case 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to ILTV or HTV, including commercially-reared poultry such as chickens, turkeys, ducks and quail.

BRIEF DESCRIPTION OF THE DRAWINGS

Preferred aspects of the invention will now be described by way of example and with reference to the accompanying drawings, in which:

FIGS. 2A–2R (on 18 sheets) shows the nucleotide sequence of the gB gene of the RB1B strain of MDV, with the numbering referring to the MDV nucleotides, the sequence of part of the HVT gB gene shown under the line, homologies indicated by vertical bars, and amino acid differences between MDV gB and HVT gB shown above the line;

FIGS. 4A–4H (on 8 sheets) shows the nucleotide sequence of most of the HVT gH gene, with the corresponding amino acid sequence shown above the line;

FIGS. 5A–5J (on 10 sheets) shows the nucleotide sequence of the HVT TK gene, with the numbering referring to the HVT nucleotides, the sequence of part of the MDV TK gene shown under the line, homologies indicated by vertical bars and amino acid differences between MDV TK and HVT TK shown above the line;

FIGS. 6A–6F (on 6 sheets) shows the nucleotide sequence of the gC gene of the RBIB strain of MDV, with corresponding amino acids shown above the line;

FIGS. 7A–7K (on 11 sheets) shows the nucleotide and predicted amino acid sequence of a 5400 base pair region of the ILTV genome containing the TK gene cluster. Amino acid sequences predicted for the products of the major open reading frames (ORFs) are indicated in the single letter code below the sequence for the strand and above the sequence for the complementary strand. The locations of potential 'TATA' boxes are underlined. ORF 4 is the ILT TK gene sequence;

FIG. 9 shows part of the nucleotide sequence of the ILTV gB gene;

Figure 10:
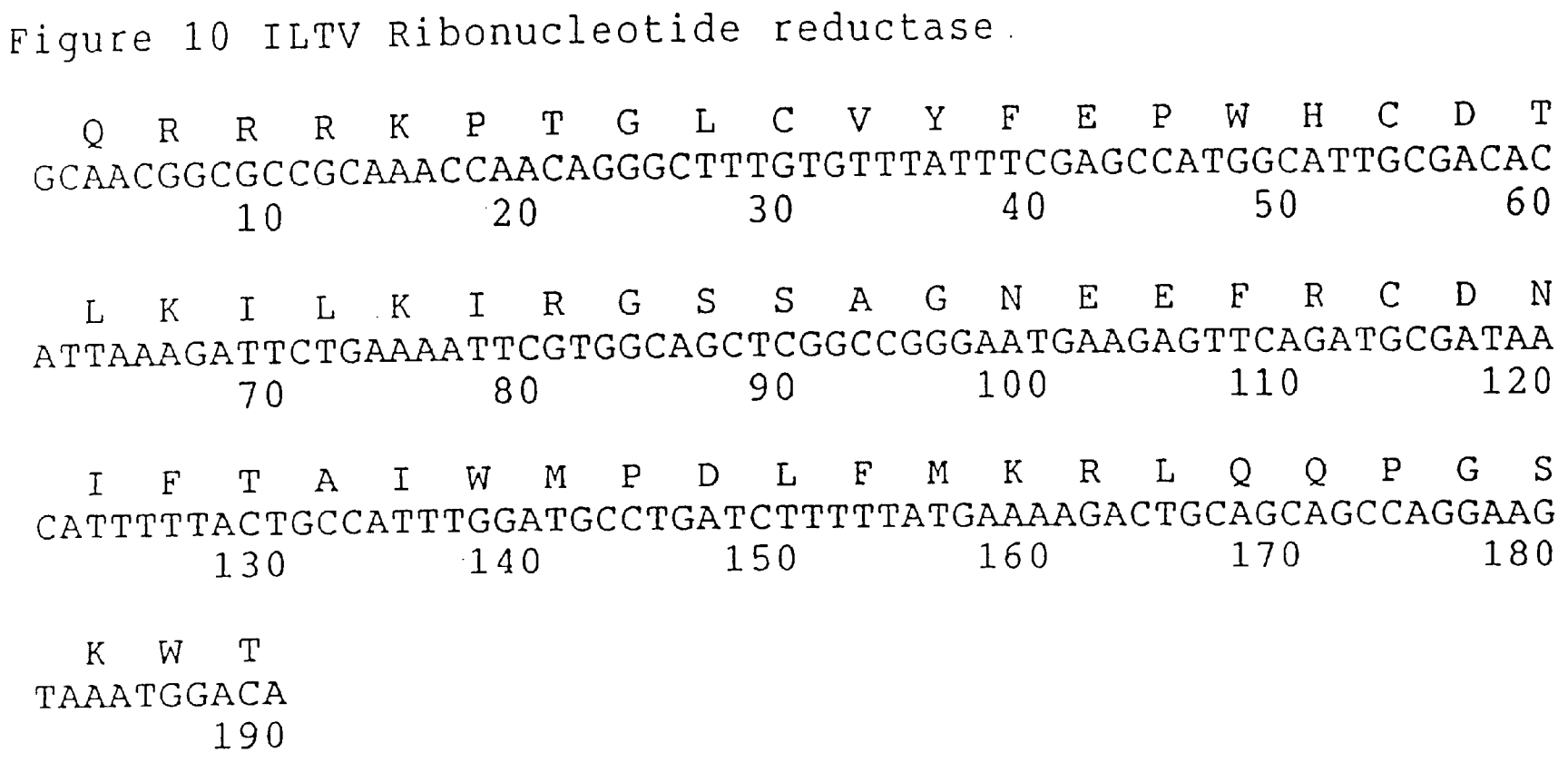

FIG. 10 shows part of the nucleotide sequence or the ILTV ribonucleotide reductase (large subunit);

FIG. 11 shows part of the nucleotide sequence of the HVT homologue of the VZV62/HSV-1 IE 175 gene;

FIG. 12 shows part of the nucleotide sequence of the HVT ribonucleotide reductase (large subunit) gene;

Figure 13A:
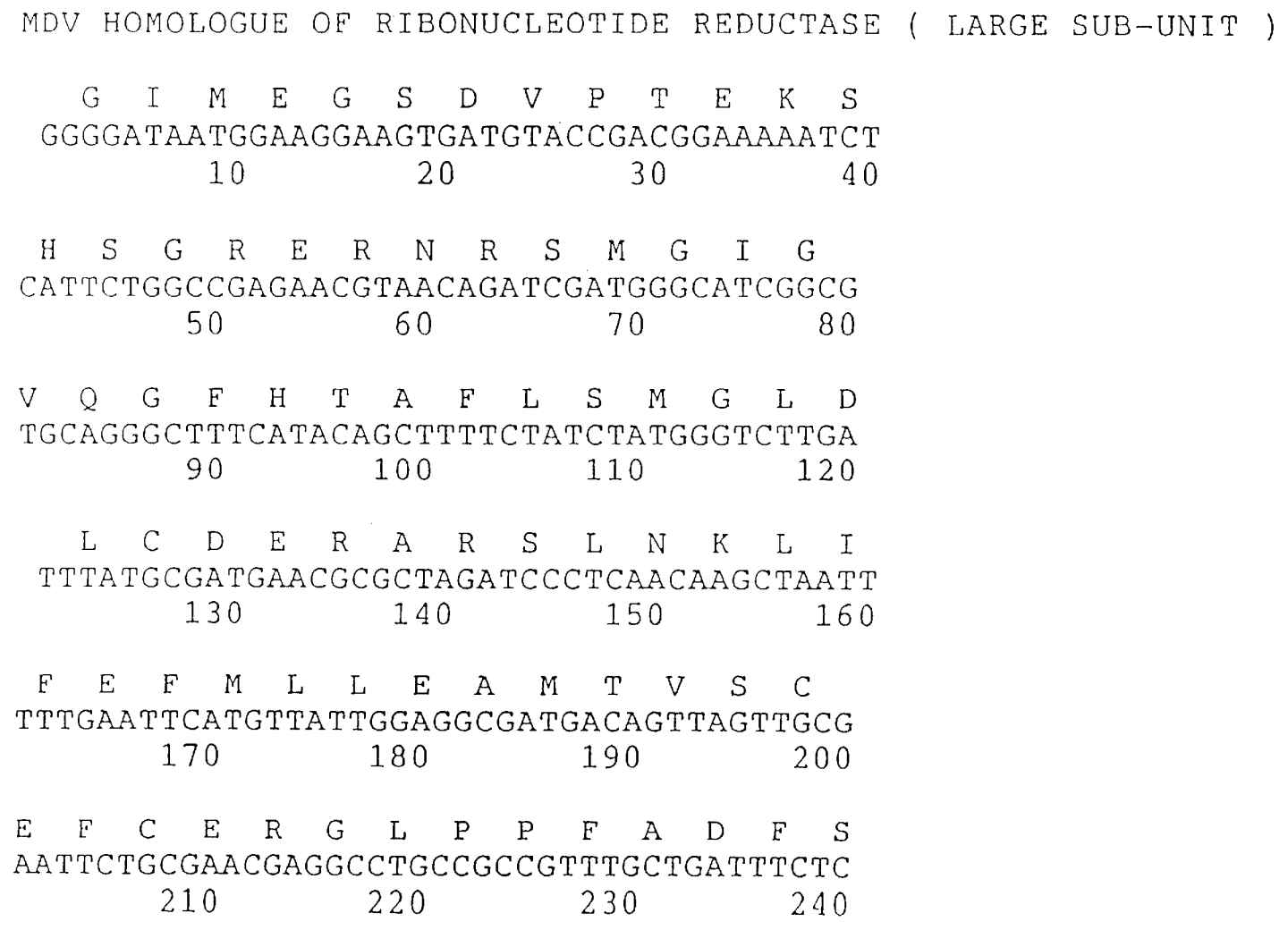

FIGS 13A–13B (on 2 sheets) shows part of the nucleotide sequence of the MDV ribonucleotide reductase (large subunit) gene;

Figure 14:
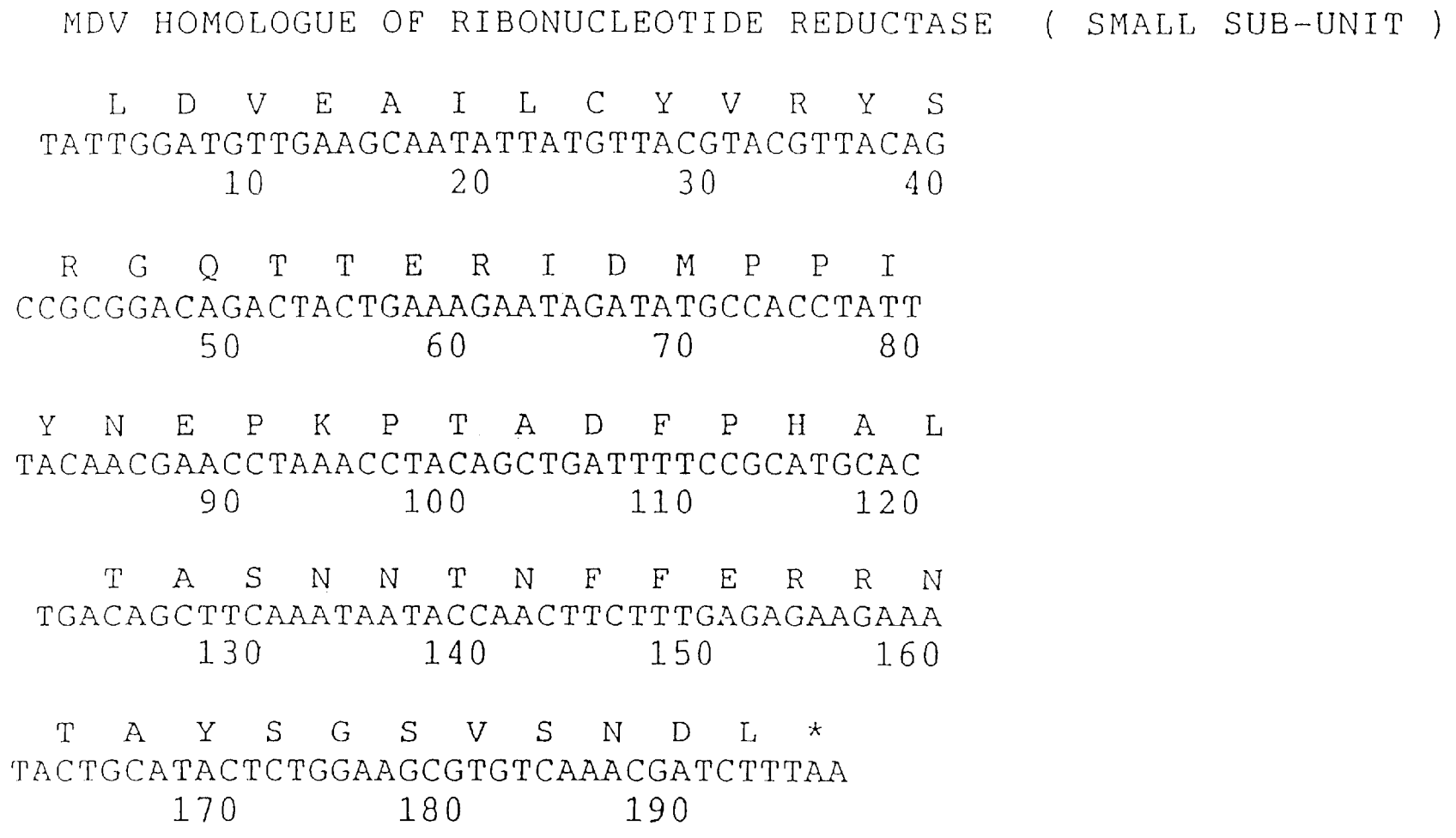

FIG. 14 shows part of the MDV homologue of ribonucleotide reductase.

FIG. 15 shows part of the nucleotide sequence of the MDV homologue of the HSV-1 IE-175 gene;

FIG. 16 shows part of the MDV homologue of the HSV-1 IE-68 gene;

EXAMPLES

General Approaches

Figure 1:
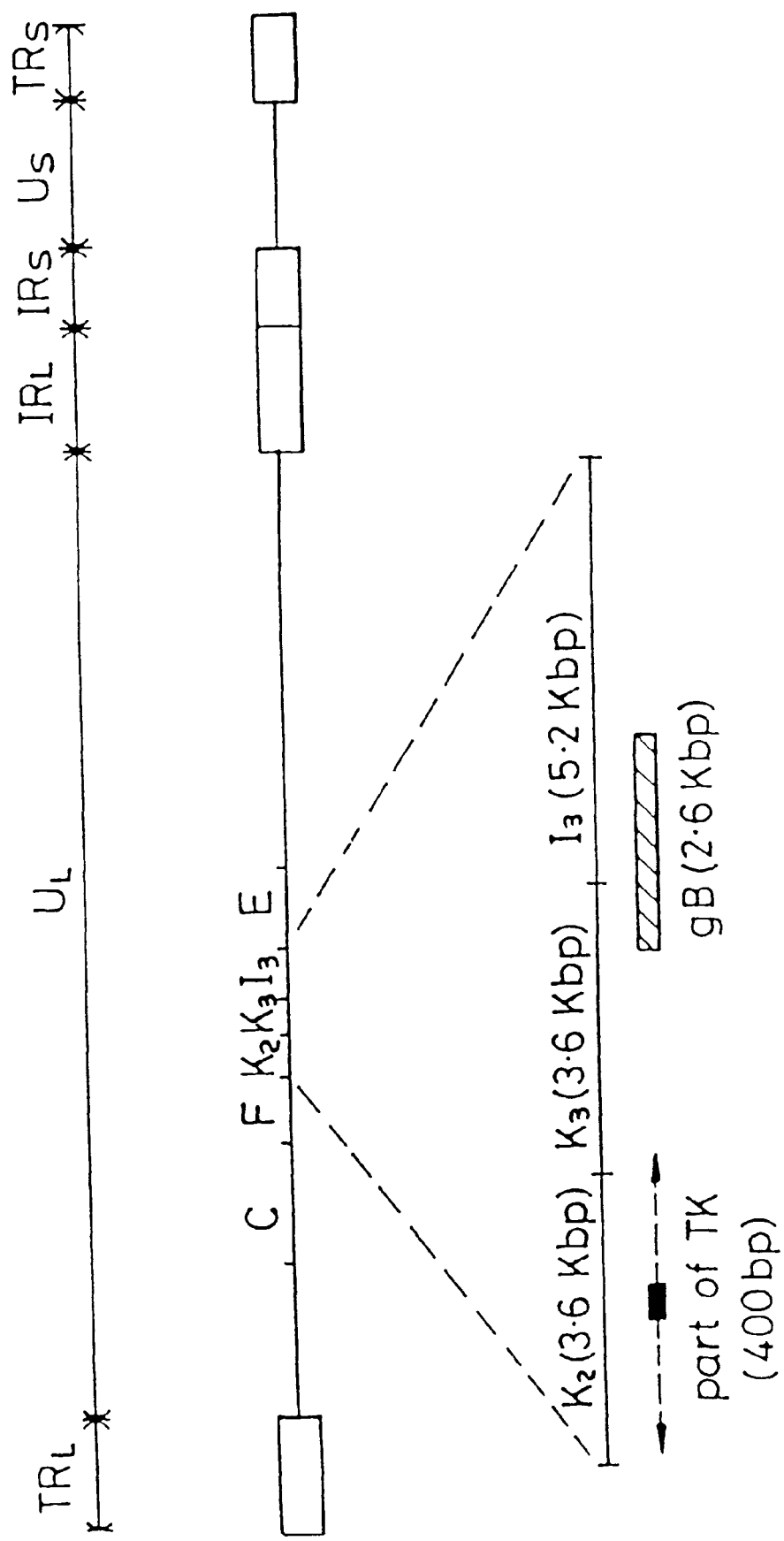
FIG. 1 is a map of the MDV genome showing in part the BamH1 site distribution and the location of the gB and TK genes.

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains. The 'highly oncogenic' strain RB1B of MDV [Schat, K. A. et al (1982) Avian Pathol. 11, 593–605] was obtained from Professor B. Calnek, Cornell University, Ithaca, U.S.A. The virus received has been plaque purified in chicken kidney veils in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525–538], obtained from the Wellcome Research Laboratories, Beckenham, Kent, had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

The Thorne strain of ILTV was passaged twice in eggs, once in chicken kidney cells (CKC) and plaque-purified three times in CKC.

Tissue culture. CEF were grown in roller bottles in 199 medium (Wellcome), supplemented with penicillin, streptomycin, Fungizone (Regd. T.M.) and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530].

Isolation of MDV DNA. Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer pH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 im 1 mM EDTA (TE).

Isolation of ILTV DNA. (a) Infected CKC were harvested 2–3 days after inoculation, washed in PBS, and resuspended in ice-cold TE by vortexing. Cells were lysed by addition of the non-ionic detergent NP40 (final 1%) vortexing and incubation on ice for 15 min. After treatment with RNAse, the preparation was centrifuged at 2000 rpm for 5 min in a bench top centrifuge (Centaur). The supernatant was collected and incubated at 37° C. for 30 min in the presence of SDS (final 1%) and proteinase K (final 0.5 mg/ml). The mixture was extracted twice with phenol-chloroform and once with chloroform and the DNA was then precipitated with ethanol and 1/10 vol of 3M sodium acetate.

(b) Viral DNA was also isolated from the media of virally infected cells in the following way. The media of infected cells were harvested at 2–3 days post infection and centrifuged at 3000 for 5 mins at 4° C. rpm in a bench centrifuge. The supernatant was collected and centrifuged at 19K rpm in an ultracentrifuge (Sorvall) for 1 hr at 4° C. The viral pellet was resuspended in TE, digested with RNAse A, then disrupted with SDS and proteinase K as described above. Finally, DNA was extracted from the disrupted virus as described above.

Cloning of MDV DNA. One fg of MDV DNA was cut with the restriction enzyme BamH1 and ligated to BamH1-cut, dephosphorylated pUC13 DNA (Pharmacia). Competent E. coli strain TG1 cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 72, 3961]. Positive colonies were cultured in small volume and plasmid DNA isolated by the procedure of Holmes, D. S. and Quigley, M. [(1981) Anal. Biochem. 114, 193–297]. The size of the inserts was determined by electrophoresis of BamH1 digests of the recombinant DNA in agarose gels. Plasmids containing MDV inserts ranging from less than 1 to 18 Kbp were obtained.

Cloning of ILTV DNA. EcoR1 and BglII libraries of ILTV DNA were obtained by cloning digests of viral DNA in pUC13 as described above.

Random sequencing of viral DNA. Sonicated fragments of viral DNA were cloned into SmaI-cut, dephosphorylated M13.mp10 (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{35}$S dATP).

The same procedure was used to sequence cloned fragments of MDV, HVT and ILTV DNA except that plaques were identified by hybridization to labelled insert so as to avoid colonies containing pUC13 fragments.

EXAMPLE 1 gB Gene of MDV

An M13 clone of HVT homologous to the gB gene of VZV and HSV hybridized to BamH1 fragment I3 of MDV (see FIG. 1). Sequencing of this fragment obtained from a BamH1 library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses such as the alignment of cysteine residues and the presence of hydrophobic sequences which are presumably capable of spanning a lipid bilayer [Pellet, P. E. et al (1985), J. Virol. 53, 243–253]. However, MDV gB has only 48% amino acid similarity with gB of HSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

EXAMPLE 2 gH Gene of HVT and gH Gene of MDV

Figure 3:
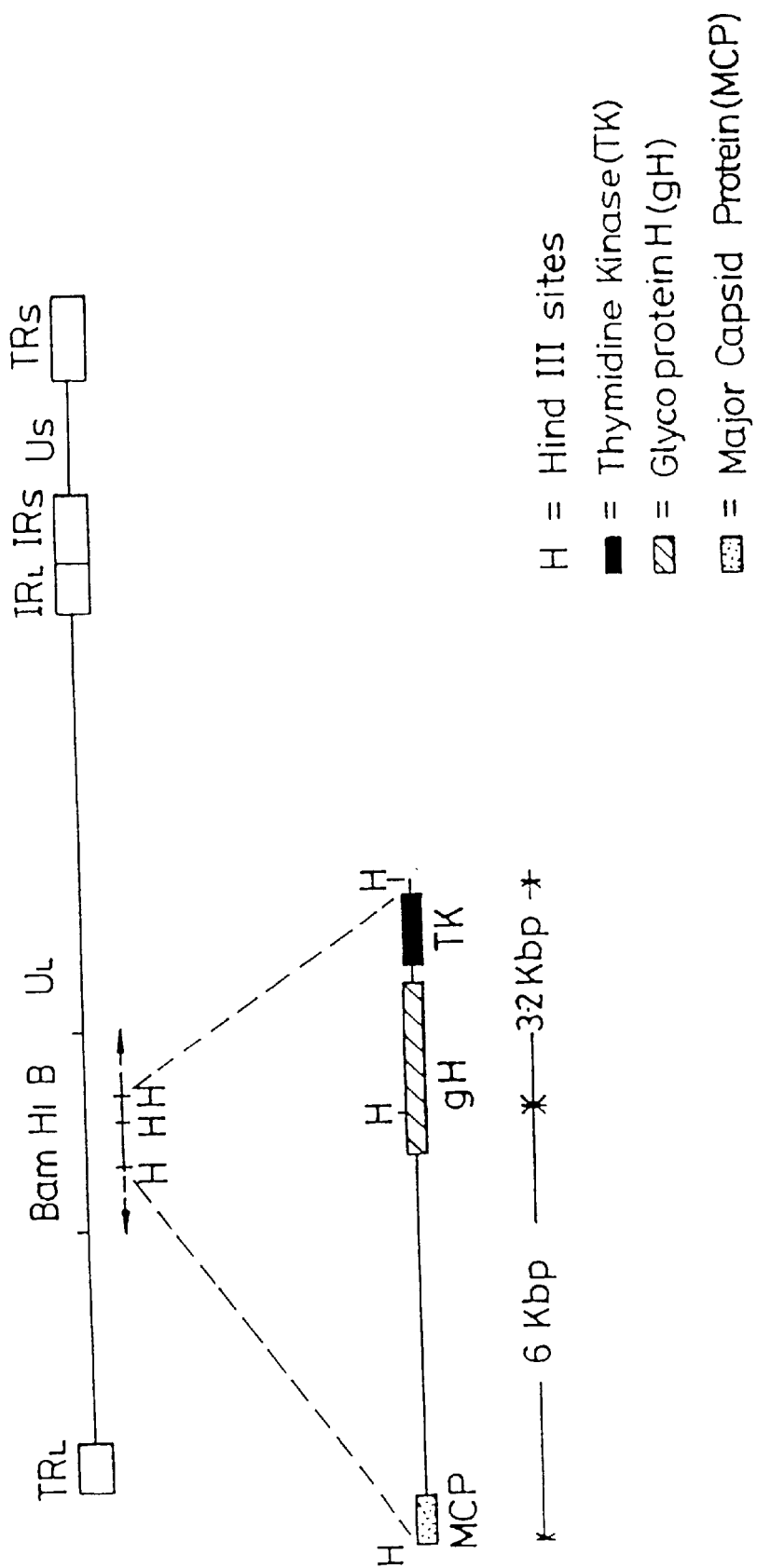
FIG. 3 is a map of the HVT genome showing the positions of the gH (hatched), TK (solid black) and major capsid protein (MCP, dotted) genes, with HindIII sites shown as "H"

An M13 clone of HVT containing sequences homologous to HSV gH was isolated during our earlier work on gene identification and mapping (Buckmaster et al (1988) as above). This clone, when used as a probe, hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24 and 20 respectively (estimated from maximised amino acid overlaps of 630, 644 and 153 respectively).

EXAMPLE 3

TK Gene of HVT and TK Gene of MDV

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamH1 K2 fragment of MDV (FIG. 1). The sequence of MDV TK gene determined so far is shown in FIG. 5. Comparison of the MDV and HVT TK sequences indicates that the two genes have approximately 60% amino acid identity (estimated from 276 amino acid overlap). By contrast, the % amino acid identities between the TK gene of HVT and the TK genes of HSV 1, VZV and EBV are only 30, 27 and 24 respectively (estimated from amino acid overlaps of 320, 332 and 193 respectively). The predicted amino acid sequences of HVT and MDV TK show characteristic ATP and/or CTP binding site motifs described for a number of virus and eukaryotic proteins that are associated with phosphorylation (Gentry, G. A. (1985) Proc. Natl. Acad. Sci. U.S.A. 82, 6815–6819). These conserved sequences are examples of useful sites for insertion and expression of foreign genes and for producing TK- deletion mutants.

EXAMPLE 4

A antigen Gene of MDV (gP57–65) (gC homologue)

The A antigen gene is of interest in vaccine development both as an immunogen (it encodes a major glycopolypeptide product) and also because we have identified it as the homologue of HSV ZC, a potential non-essential region. The A antigen gene was mapped within the BamH1 B fragment of MDV (Isfort et al 1987), and the nucleotide sequence determined for the GA strain of MDV (Coussens and Velicer, Abstract OP18.51, VII International Congress of Virology, Aug. 9–14, (1987) Edmonton, Canada; J. Virol. 62, 2373–2379). During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoR1 cleaved pUC13 vector by standard protocols. One plasmid (pMB419) was sequenced by the M13 dideoxynucleotide method. The sequence of the MDV RB1B A antigen and the predicted amino acid sequence of the protein are presented in FIG. 6. The A antigen regions of MDV and HTV are non-essential genes and they can therefore be used as sites in MDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.

2) On conducting a similarity search it became clear that the MDV A antigen gene is the homologue of HSV-gC and PRV gpIII glycoproteins. Both of these homologous genes are known to be non-essential [for the HSV homologue, see Rosenthal et al (1987) J. Virol. 61, 2438–2447].

3) Strains of MDV lacking A antigen as judged by agar gel diffusion tests [Churchill, A. E. et al (1969) J. gen. Virol. 4, 557–564] or producing low levels using the more sensitive 2D radio-immunoprecipitation (van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

STRATEGIES FOR INTRODUCING GENES INTO HVT AND ILTV VECTORS

Two possibilities can be envisaged. 1) Insertion into non-essential genes of the vector. 2) Substitution of foreign gene for corresponding gene of the vector. This would be possible only in regions which already have substantial homology as may be the case between some genes of MDV and HVT.

EXAMPLE 5

Insertion into Non-essential Genes of HVT, ILTV or MDV (a) Insertion at the TK locus of the vector.

1) HVT, ILTV or MDV may be used as vectors for insertion and expression of avian herpesvirus genes. In particular gB, gD, gH or gC of RB1B MDV may be inserted into ILTV. Also gB and BS-17 of ILTV may be inserted into HVT or MDV. One may use the promoter associated with the inserted gene or use heterologous promoters, including those of a different class of genes (for example the immediate early promoter to optimise expression of gB).

2) ILTV may be used as a general vector for the insertion and expression of genes unrelated to avian herpes viruses and likely to require manipulation of promoters for optimal expression.

The procedure to be used for gene insertion is substantially as described previously for the insertion of hepatitis antigen in HSV [Shih et al, 1984 as above].

MDV and HVT DNA obtained as described above is infectious provided that precautions are taken not to shear the DNA during extraction. Calcium phosphate precipitates of viral DNA prepared as described by Stow and Wilkie [(1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinised, replated (1:1 or 1:2) in 199 medium (Wellcome) containing 2 to 4% calf serum and incubated at 37° C. until plaques developed, usually after 4 to 5 days. Approximately 200 plaques may be obtained per μg of HVT DNA and approximately 50 per μg of MDV DNA.

Restriction enzyme sites than could be used for the insertion of foreign antigens into the TK of HVT strain Fc-126 include: BanII, Bsp1286, DraIII, EcoRI, HincII, HpaI, NheI and NspbII.

Some of these enzymes also have sites in the plasmid vector into which the virus DNA fragments are cloned. Thus in order to linearize the clone DNA without also cutting within the vector, partial digests may be carried out.

None of the above enzymes should cause any disruption to flanking gene, HSV-1 homologues of which are known to play an important role in virus multiplication.

For homologous recombination and isolation of recombinant virus, genes of interest are inserted within non-essential genes such as TK or gC and co-transfected with wild-type viral DNA at molar ratios ranging from 10:1 to 2:1 as described above. Alternatively, intact wild-type virus may be used for co-infection.

Virus recombination may be detected by 'plaque lifts' which involve transfer of infected cells and released virus which have adhered to the agar overlay to nitrocellulose and hybridization of the denatured DNA released from the cells and virus to suitable probes as described by Villareal, L. et al (1977) Science 196, 183–185. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system such as labelled protein A or phosphatase conjugated anti-globulin antibody.

The gene of interest with appropriate promoters is first inserted within the cloned TK gene (FIG. 7). The recombinant DNA is then co-transfected with infectious DNA of the vector in chick embryo fibroblasts or chicken kidney cells and TK- virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus the use of an immediate early promoter may allow expression in latently infected cells.

(b) Insertion at the gC locus of the vector.

Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or with specific antibody allows the isolation of recombinants.

EXAMPLE 6

Substitution of ILTV Genes for Their Homologues in HVT

Substitution may be achieved by co-transfection of cloned ILTV sequences and infectious HVT DNA as described in Example 5. Substitution of genes derived from ILTV for their counterparts in HVT may be effected.

Recombinants expressing ILTV sequences and epitopes may be detected using ILTV-specific monoclonal antibodies or anti-peptide antibodies raised against unique ILTV sequences as described above.

The advantage of this procedure is that it is relatively simple and does not require manipulation of promoters. However, it may be limited to genes which share substantial homology.

EXAMPLE 7

Strategies for Obtaining TK- mutants of ILTV

Figure 8:
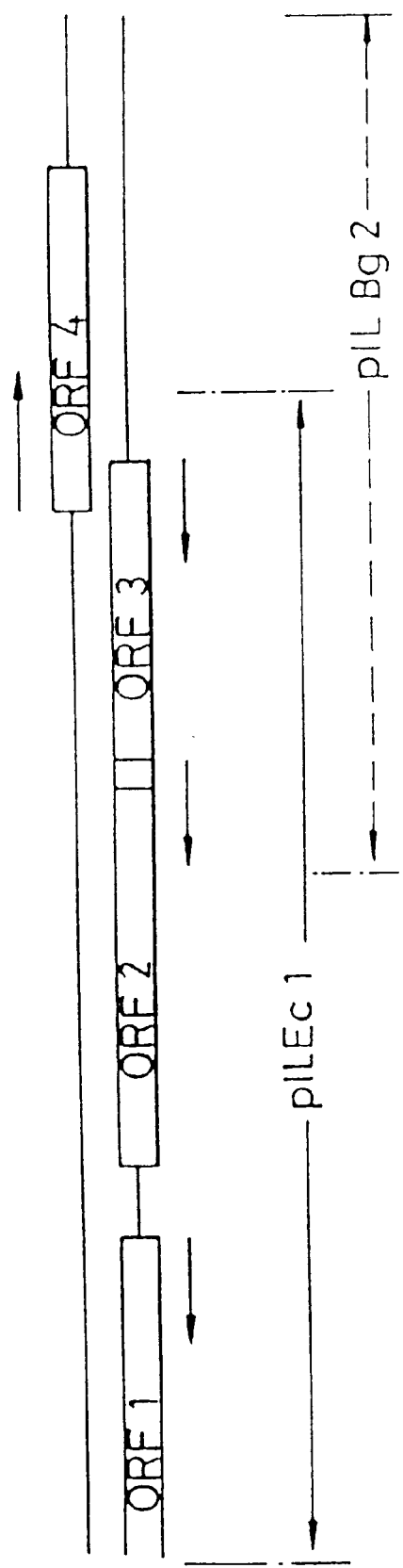
FIG. 8 is a representation of the gene organisation in the TK-containing part of the ILTV genome. Overlapping pUC 13 plasmid clones containing the EcoR1 (pILEc1) and BglII (pILBg2) generated fragments of ILTV DNA are indicated. Open reading frames (ORFs) are depicted as open boxes with the direction of transcription indicated by the arrow.
Figure 17:
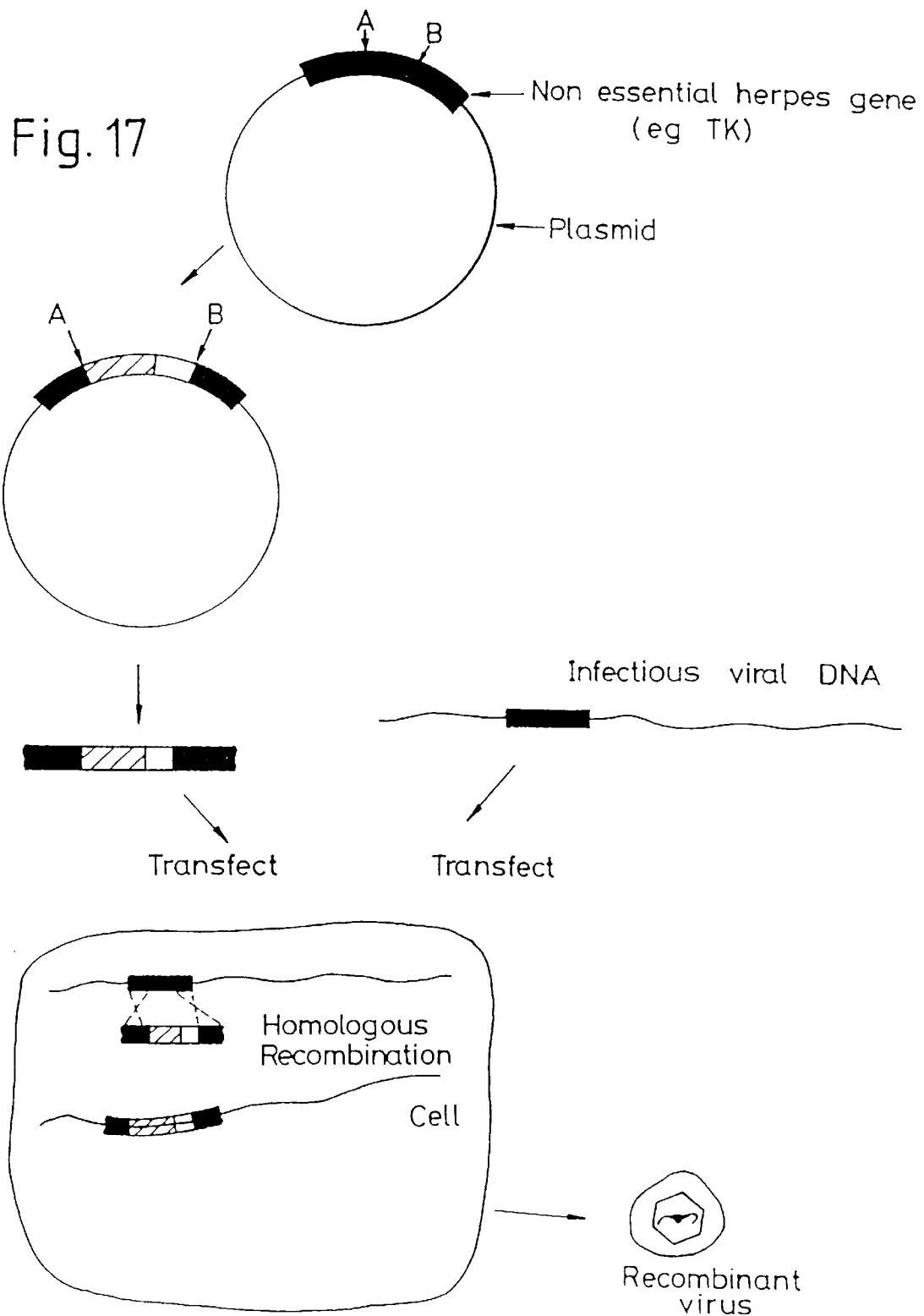
FIG. 17 is a schematic representation of homologous recombination at a non-essential region of a viral genome and a homologous region of DNA cloned within a plasmid vector.
Figure 18:
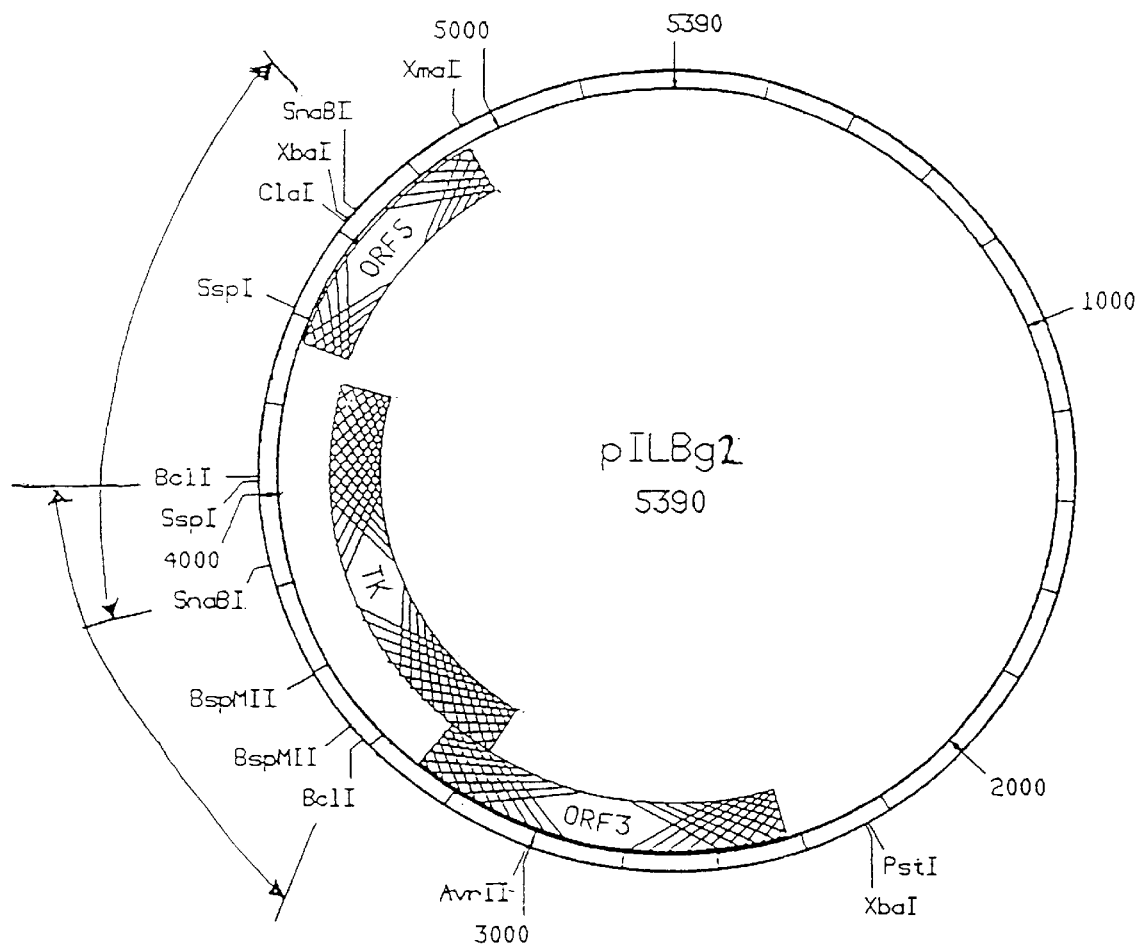
FIG. 18 is a map of plasmid pILBg2, showing restriction sites and the locations of the TK gene and ORFs 3 and 5.

Deletion mutants. Deletions may be introduced within any suitable part of the gene, for example the domains of the gene that are required for its function as a phosphorylating enzyme such as ATP and CTP binding sites. This may be achieved by restriction enzyme digestion, for example with SnaB1 or BclI, and religation of appropriate fragments followed by co-transfection with infectious viral DNA or transfection into virally-infected cells. Reference may be made to FIGS. 7 and 8, and to the map of plasmid pILBg2 (FIG. 18), in choosing restriction enzymes and so on. TX- virus may be selected in the presence of acyclovir [Ross, N. (1985) as above] or FMAU [Schat, K. A. et al (1984) as above]. Plaque-purified clones may then be tested for the absence of the deleted portion of the TX gene by hybridization.

The deletion mutants of ILTV may be used themselves as attenuated viruses for vaccine preparation, or may have sequences for heterologous antigens inserted.

Insertional mutants. A functional β-galactosidase gene under the control of a herpesvirus promoter or any other suitable sequence or a single base is first introduced in a domain of the TX gene which is essential for TK activity. The recombinant DNA is then co-transfected with infectious viral DNA or transfected into virally-infected cells to allow homologous recombination to occur. Selection in the presence of acylovir or FMAU will yield TK- insertional mutants. If a β-galactosidase gene is introduced, mutants can be detected by the production of blue plaques in the presence of X-gal.

The TX gene and surrounding sequences may be sub-cloned into another suitable vector if necessary.

EXAMPLE 8

Insertion of MDV RB1B gB Gene into HVT (Not within the scope of the invention, but illustrates an analogous technique).

The HVT TK gene is cloned in the plasmid vector pUC13 to generate a plasmid, which may be termed pTK1B. This plasmid is linearised with, for example, the restriction endonuclease Rsr II which cleaves the plasmid only within the TX gene (nucleotide position 197 in FIG. 5, enzyme recognition sequence CGGACCG). The "sticky" ends thus generated are end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which were termed RB1B-BamH1-$I_3$ and RB1B-BamH1-$K_3$. (Note $I_3$ had lost one BamH1 site during cloning.) To generate a complete gB copy on one plasmid, both plasmids were cleaved with BamH1 and the fragments ligated. However, the complete gB gene was later obtained independently on an EcoRI/SalI fragment. Ross et al, J. gen. Virol (1989) 70, 1789–1804 provides further information regarding the manipulation of viral genes. Recombinants containing the desired configuration can be identified by restriction enzyme analysis of plasmid DNA's.

The recombinant plasmid is then cleaved with EcoR1, the ends are repaired and the plasmid is cloned into PTK1B prepared as above. The recombinant plasmid is then introduced into cells containing HVT virus (viral DNA) and homologous recombination will introduce the gB gene into the TK gene. HVT viral recombinants can be selected with acyclovir or FMAU or alternatively detected with labelled gB probes.

EXAMPLE 9

RB1B gC (A antigen) Gene into HVT

Blunt ended PTK1B is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTK1B as in Example 8. (The cloning can be verified by analysis of the resulting clones with restriction enzymes, probing with radio-actively labelled fragments, or DNA sequencing, or any combination of these).

The resulting plasmid with the RB1B gC gene cloned into the HVT TK gene can then be introduced into the HVT genome by transfecting the plasmid into HVT-infected cells using calcium phosphate precipitation or electroporation. Homologous recombination, involving cross-overs either side of the gC gene, between the HVT virus and the flanking sequences of the HVT TK plasmid will carry the RB1B gC gene into the HVT viral genome. Viral recombinants can be selected for (as they are TK-) or identified (eg by probing) as described above.

In analogous ways, the sequence information given above and in the Figures can be used to design cloning strategies for the insertion of these genes and others into the non-essential genes of the ILTV described here or to generate combinations of antigen genes into ILTV.

We claim:

1. A non-naturally occurring nucleotide fragment comprising the nucleotide sequence, as shown in FIG. 9.

2. A viral vector selected from the group consisting of Marek's Disease Virus (MDV) and Herpesvirus of Turkeys (HVT) which viral vector contains the non-naturally occurring nucleotide fragment of claim 1 inserted into the viral vector at a site which is not essential for infectivity and replication.

3. A viral vector according to claim 2 wherein the viral vector is MDV which viral vector contains the naturally occurring nucleotide sequence as shown in FIG. 9.

4. A viral vector according to claim 2 wherein the viral vector is HVT which viral vector contains the naturally occurring nucleotide sequence as shown in FIG. 9.

* * * * *